(12) United States Patent
Klaus et al.

(10) Patent No.: US 6,469,017 B1
(45) Date of Patent: *Oct. 22, 2002

(54) METHOD OF INHIBITING INTERLEUKIN-12 SIGNALING

(75) Inventors: Stephen J. Klaus, Seattle; J. Peter Klein, Vashon Island; Anil M. Kumar, Mercer Island, all of WA (US)

(73) Assignee: Cell Therapeutics, Inc., Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/008,020

(22) Filed: Jan. 16, 1998

(51) Int. Cl.$^7$ ................................ A61K 31/52
(52) U.S. Cl. .................... 514/263; 514/267; 514/270; 514/271
(58) Field of Search ........................ 514/263

(56) References Cited

U.S. PATENT DOCUMENTS

| 4,515,795 A | * | 5/1985 | Hinze et al. | ................. 514/263 |
| 5,629,423 A | | 5/1997 | Klein et al. | ..................... 544/48 |
| 5,648,357 A | | 7/1997 | Bianco et al. | ............... 514/263 |

OTHER PUBLICATIONS

Heremans et al., *Lymphokine Research*, "The Role of Cytokines in Various Animal Models of Inflammation," vol. 8, No. 3, pp. 329–333, 1989.

Klaus et al., *The Journal of Immunology*, "Inducible Cell Contact Signals Regulate Early Activation Gene Expression During B–T Lymphocyte Collaboration," vol. 149, No. 6, pp. 1867–1875, Sep. 1992.

LeGros et al., *The Journal of Experimental Medicine*, "Generation of Interleukin 4 (IL–4)–producing Cells In Vivo and In Vitro: IL–2 and IL–4 Are Required For In Vitro Generation of IL–4 producing Cells," vol. 172, pp. 921–929, Sep. 1990.

Moller et al., *Immunology*, "Inhibition of Human Interleukin–12 Production by Pentoxifylline," vol. 91, pp. 197–203, 1997.

Owens et al., *Neurologic Clinics*, The Immunology of Multiple Sclerosis and its Animal Model, Experimental Allergic Encephalomyelitis, vol. 13, No. 1, pp. 51–73, Feb. 1995.

R&D Systems Catalog, pp. 67–69, 1995.

Racke et al., *Journal of Neuroimmunology*, "Long–term treatment of chronic relapsing experimental allergic Encephalomyelitis by transforming growth factor–β2," vol. 46, pp. 175–184, 1993.

*Remington's Pharmaceutical Sciences*, Chapters 83–92, pp. 1519–1714, 1990.

Rott et al., *Eur. J. Immunol*, "Phosphodiesterase Inhibitor Pentoxifylline, a Selective Suppressor of T helper Type 1–But Not Type 2–Associated Lymphokine Production, Prevents Induction of Experimental Autoimmune Encephalomyelitis in Lewis Rats," vol. 23, pp. 1745–1751, 1993.

Trembleau et al., *Immunology Today*, "The Role of IL–12 in the Induction of Organ–specific Autoimmune Diseases," vol. 16, No. 8, pp. 383–386, 1995.

Trinchieri, G., *Annu Rev. Immunol.*, "Interleukin–12: A Proinflammatory Cytokine With Immunoregulatory Functions That Bridge Innate Resistance and Antigen–Specific Adaptive Immunity," vol. 13, pp. 251–276, 1995.

\* cited by examiner

*Primary Examiner*—Theodore J. Criares
(74) *Attorney, Agent, or Firm*—Foley & Lardner

(57) ABSTRACT

A method for blocking IL-12 signaling by administration of the following compound:

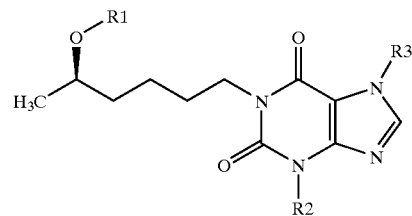

wherein, $R_1$ is H, $CH_3$, sulfate, phosphate, or salt thereof; $R_2$ is alkyl ($C_{1-12}$), alkoxyalkyl ($C_{1-11}$), dialkoxyalkyl, $CH_2C_6H_5$, —$CH_2$-furan, biotin; and $R_3$ is H, $CH_3$ or $CH_2C_6H_5$.

11 Claims, 22 Drawing Sheets

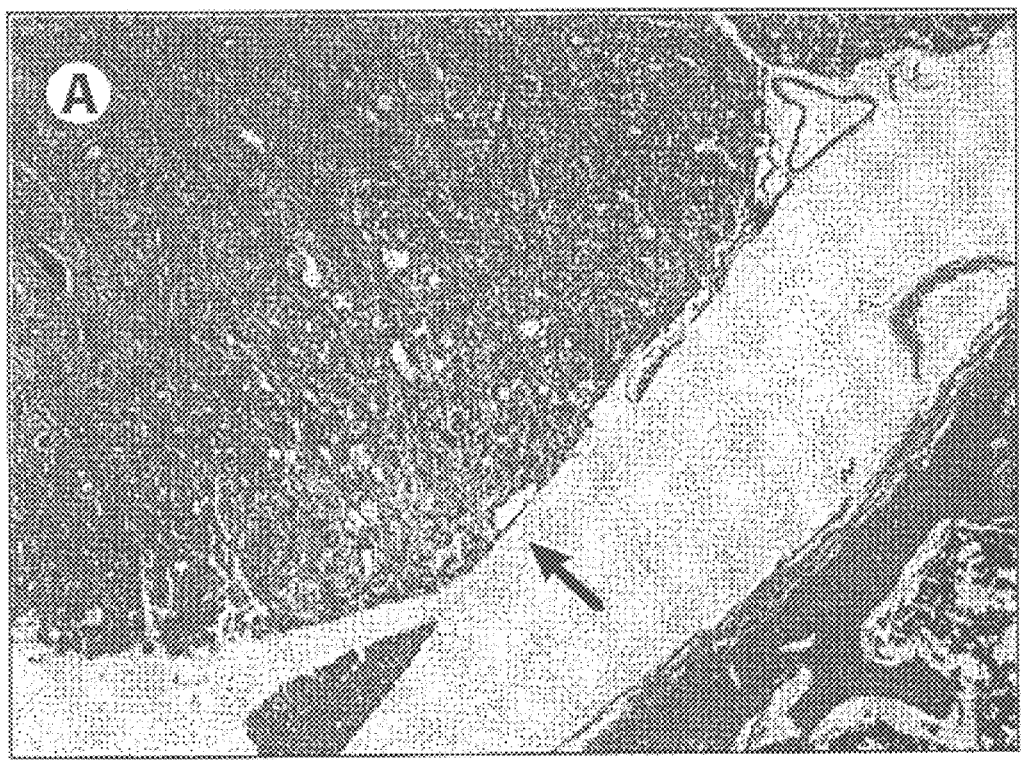
Fig. 3b-A

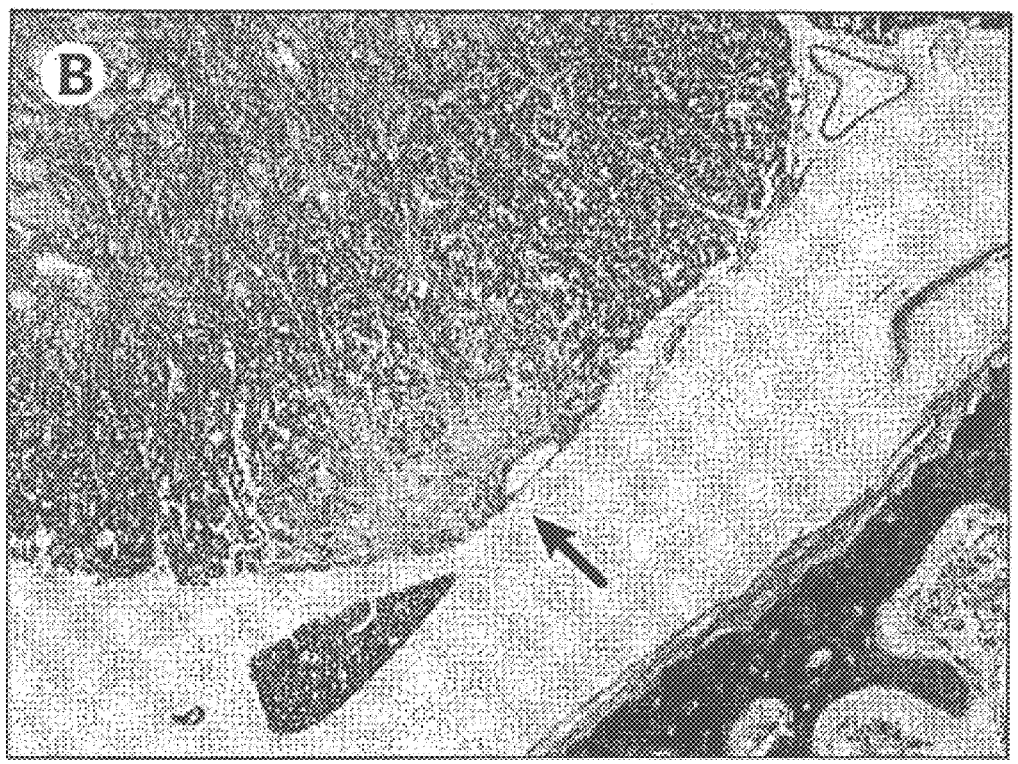
Fig. 3b-B

CT-1501R
Fig. 3b-C

CT-1501R
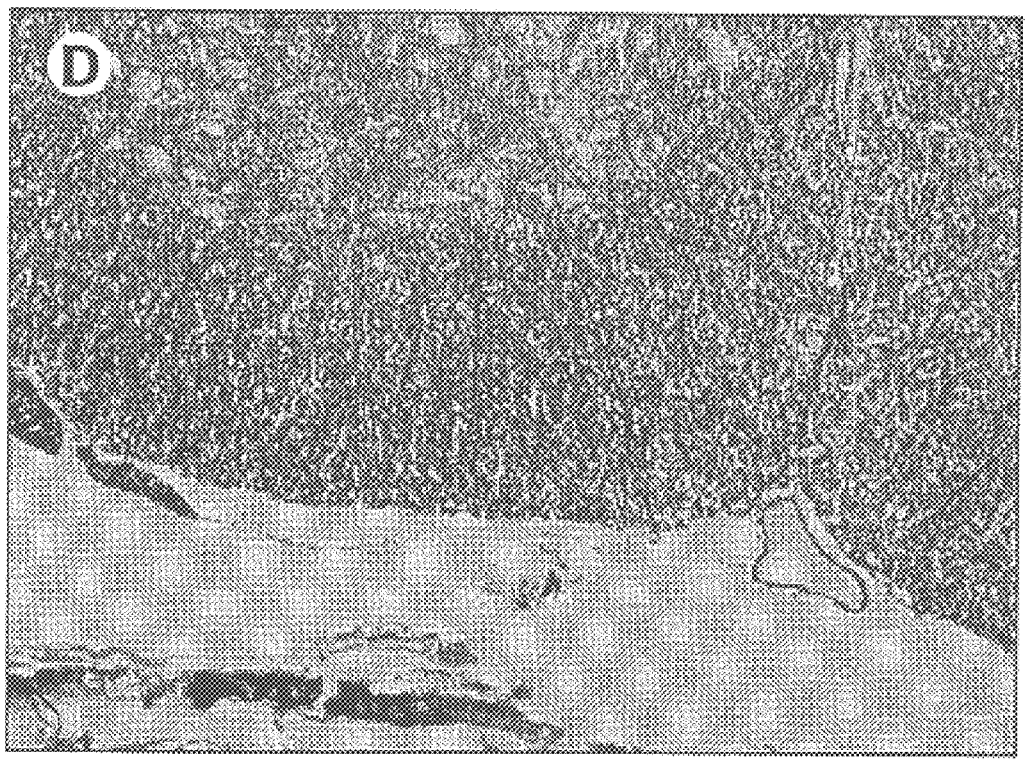
Fig. 3b-D

METHOD OF INHIBITING INTERLEUKIN-12 SIGNALING

FIELD OF THE INVENTION

The present invention relates to a method of inhibiting Interleukin ("IL")-12 signaling in inflammatory disorders, more particularly in inhibiting IL-12 signaling in CD4+ Th1 cell-mediated inflammatory disorders.

BACKGROUND OF THE INVENTION

Inflammatory responses are a component of the pathogenesis of many vertebrate disorders, including those in man. In its broadest meaning, the term "inflammation" denotes local as well as systemic responses. Increased blood flow, vasodilation, fluid transudation from the vessels, infiltration of the tissues by leukocytes and, in some severe cases, intravascular thrombosis, damage to the blood vessels and extravasation of blood characterize local inflammation. The systemic inflammatory response, also denoted as an acute phase response, is characterized by various reactions including, for example, fever, leukocytosis and release of acute phase reactants into the serum. In severe cases, shock and death may occur. Heremans et al., *Lymphokine Research* 8(3): 329–333 (1989).

The inflammatory response is controlled by a variety of cellular events. Cytokines are primary factors in the cascade of events that regulate inflammatory responses. Some cytokines induce or release other known mediators of inflammation. These systems are controlled by related feed-back mechanisms. Thus, inflammatory responses are not due to a single cytokine being released in large quantities, but rather to a set of cytokines acting collectively via a network of intercellular signals to incite the inflammatory response. Ibid.

One particular cytokine, IL-12, also known as natural killer cell stimulatory factor ("NKSF") and cytotoxic lymphocyte maturation factor ("CLMF"), is a potent immunoregulatory molecule which plays a role in a wide range of diseases. In particular, IL-12 is known to play a specific role in diseases exhibiting an inflammatory component, namely, diseases that exhibit cell-mediated inflammatory responses, such as, multiple sclerosis, diabetes, and chronic inflammatory bowel disease. Ibid.

IL-12 is produced by phagocytic cells, such as monocytes/ macrophages, B-cells and other antigen-presenting cells ("APC"). Functionally, IL-12 affects both natural killer ("NK") and T-lymphocytes ("T cells"), and stimulates IFN-γ production by both of these cell types. For example, in NK cells, IL-12 stimulates: NK cell proliferation, membrane surface antigen up-regulation, LAK cell generation and NK cell activity elevation; induces IFN-γ and TNF-α production and the growth and expansion of either resting or IL-2 activated NK cells; and increases soluble p55 and soluble p75 TNF receptor production and NK cell cytotoxicity. R&D Systems Catalog, pp. 67–69 (1995).

T-cell recognition of antigen occurs via interaction of a heterodimeric (alpha/beta, or gamma/delta) receptor with short peptide antigenic determinants that are associated with major histocompatibility complex ("MHC") molecules. T cells can be divided broadly into two functional categories by the presence of two mutually exclusive antigens on their cell surface, CD4 (helper) and CD8 (cytotoxic). The CD4 and CD8 antigens regulate T-cell interaction with MHC and their mutually exclusive expression derives from their strict specificity for MHC. Class II MHC-restricted T cells are primarily CD4+ and class I MHC-restricted T-cells are CD8+. The T cells further differentiate into helper, cytotoxic and suppressor cells. As mentioned above, IL-12 also affects T-cells. As mentioned above, IL-12 also affects T cells, including stimulation of T cell IFN-γ production in response to antigen. T cells are broadly divided into two major subsets based on the expression of two mutually exclusive surface antigens, namely CD4 and CD8. While CD8+ T cells are associated with cytotoxicity functions, CD4+ T cells are associated with helper function and secrete various cytokines which regulate and modulate immune responses. CD4+ T cells can be further subdivided into T helper 1 (Th1) and T helper 2 (Th2) subsets, according to the profile of cytokines they secrete. Therefore, Th1 cells produce predominantly inflammatory cytokines, including IL-2, TNF-α and IFN-γ, while Th2 cells produce anti-inflammatory cytokines such as IL-4, IL-5, IL-10, and IL-13 which are linked to B cell growth and differentiation.

The Th1 and Th2 CD4+ T cell subsets are derived from a common progenitor cell, termed Th0 cells. During initial encounter with antigen, the differentiation into Th1 and Th2 is controlled by the opposing actions of two key cytokines, namely IL-12 and IL-4, which induce the differentiation of Th0 into Th1 and Th2, respectively. The development of Th1 and Th2 cells is primarily influenced by the cytokine milieu during the initial phase of the immune response, in which IL-12 and IL-4, respectively, play decisive roles. The cytokines produced by each Th-cell phenotype are inhibitory for the opposing phenotype. For example, Th1 cytokines enhance cell-mediated immunities and inhibit humoral immunity. Th2 cytokines enhance humoral immunity and inhibit cell-mediated immunities. Trembleau et. al., *Immunology Today* 16(8): 383–386 (1995).

Furthermore, CD4+ Th1 cells play a role in the pathogenesis of immunological disorders. These cells primarily secrete cytokines associated with inflammation such as IFN-γ, TNF-α, TNF-β, and IL-2. IFN-γ is an important component of the inflammatory response and resultant pathology of those diseases exhibiting an inflammatory response. Heremans, et al. In addition to its role in inflammatory response, IFN-γ also contributes to phagocytic cell activation (i.e., macrophage activation), and up-regulation of MHC expression on the surface of antigen-presenting cells ("APC") and other cells. Furthermore, this cytokine is implicated generally in inflammatory immune responses, and in autoimmune diseases, such as MS, specifically. Owens et al., *Neurologic Clinics,* Volume 13(1):51–73 (1995). Furthermore, steroid treatment broadly attenuates cytokine production, but it cannot modulate it selectively, e.g., just the Th0, the Th1 or the Th2 pathways.

IL-12 plays a role in the induction of Th1-cell-mediated autoimmunity. Recent evidence points to a critical role for IL-12 in the pathogenesis of rodent models of Th1-mediated autoimmune diseases such as type-1 diabetes, multiple sclerosis, rheumatoid arthritis, inflammatory bowel disease, and acute graft-versus-host disease. Thus, Th1 cells are considered to be involved in the induction of experimental autoimmune diseases. Evidence for this is based on adoptive transfer experiments demonstrating the CD4+ cells producing Th1-type lymphokines can transfer disease, as shown in models of experimental autoimmune disease, such as experimental allergic encephalomyelitis ("EAE") (also known as experimental allergic encephalitis) and insulin-dependent diabetes mellitus ("IDDM"). Trinchieri, *Annu. Rev. Immunol.* 13(1):251–276 (1995). EAE is an inflammatory T cell mediated, paralytic, demyelinating, autoimmune disease that can be induced in a number of rodents as well as primates. Owens et al. One of the ways that EAE can be induced is by immunization of animals with myelin basic protein ("MBP"). Ibid. Administration of IL-12 induces rapid onset of IDDM in 100% of NOD female mice. Trinchieri. Thus, one goal of immunotherapy has been to limit the inflammatory response while leaving the specificity of the immune system, deemed necessary for host protection, intact.

For example, steroid therapy is the most common treatment for one such IL-12 mediated disease, Multiple Sclerosis ("MS"), particularly, corticosteroids. This suggests that steroids alter the trafficking of cells into the brain or reduce the secretion of cytokines by inflammatory cells in areas of inflammation. Ibid. Although their effect in reversing some of the acute symptoms of autoimmune disease, such as MS, are well known, their side effects have precluded long-term use. Ibid.

Other treatments that target immune system components include lymphocyte cytotoxic drugs such as cyclophosphamide and azathioprine. These drugs act as sledgehammers, suppressing the entire immune system, with the problems that attend broad-spectrum immunosuppression. The same problems also are likely with newer therapies such as cyclosporine, anti-CD4 monoclonal antibodies, and others. Other treatments for IL-12 mediated diseases, including MS, can involve the administration of anti-IL-12 antagonists such as antibodies. Anti-IL-12 antibodies have been shown to inhibit the development of IDDM and EAE. Trinichieri. However, antibody based immunotherapy may result in immune complex formation and deposition, thus leading to glomerulonephritis, vasculitis and arthritis.

Still other treatments for IL-12 mediated diseases involve the phosphodiesterase inhibitor, pentoxyifylline ("PTX"). For example, PTX has been used as an anti-inflammatory agent in T-cell mediated autoimmune disease, exemplified by the animal model of EAE in Lewis rats. Rott et al., *Eur. J. Immunol.* 23:1745–1751, (1993). EAE in rodents is a well-characterized animal model for the study of demyelinating inflammation in the central nervous system ("CNS") and autoimmune diseases in general, including MS. Ibid. PTX is able to suppress efficiently the activation of Th1 cells in vitro and in vivo without resulting in an overall immunosuppression or causing obvious severe side effects. Ibid. Pretreatment with IFN-γ reduced the suppressive effects of pentoxifylline on production of IL-12, and thus, is not a suitable therapy when there occurs an ongoing production of IFN-γ. Moller et al., *Immunology* 91:197–203 (1997).

Thus, there remains a need for compounds and methods that singularly inhibit the deleterious effects of inflammatory responses mediated by specific cytokines, such as IL-12, without effecting the other components of the immune system deemed necessary for protection of the host. The present invention fulfills this need and provides for further related advantages.

SUMMARY OF THE INVENTION

It is an object of the present invention to provide a method of inhibiting IL-12 signaling in a mammal having a CD4+ Th1 cell-mediated inflammatory response by administering a signal inhibiting amount of the compound of the following formula:

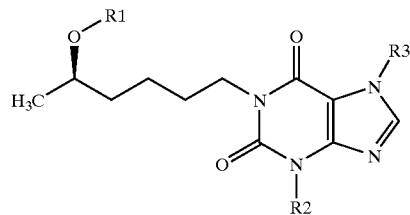

wherein, $R_1$ is H, $CH_3$, sulfate, phosphate, or salt thereof; $R_2$ is alkyl ($C_{1-12}$), alkoxyalkyl ($C_{1-11}$), dialkoxyalkyl, $CH_2C_6H_5$, —$CH_2$-furan, biotin; and $R_3$ is H, $CH_3$ or $CH_2C_6H_5$. In accomplishing this and other objectives, the present invention provides a method for affecting The inflammatory response associated with CD4+ Th1 cell-mediated diseases; without affecting The other components of the immune system, deemed necessary for host protection. The present methods short-circuit the inflammatory cascade by inhibiting IL-12-dependent Th1 development, emphasizing the inventive methods importance in disease therapy by inhibiting IL-12 signaling in the regulation of CD4+ Th1-mediated inflammatory disorders.

BRIEF DESCRIPTION OF THE DRAWINGS

These and other features, aspects, and advantages of the present invention will become better understood with reference to the following description, appended, and accompanying drawings where:

FIGS. 3a and 3b show the ability of CT 1501R to prevent CNS inflammation and demyelination in an EAE model.

DETAILED DESCRIPTION OF PREFERRED EMBODIMENTS

Figure 1:
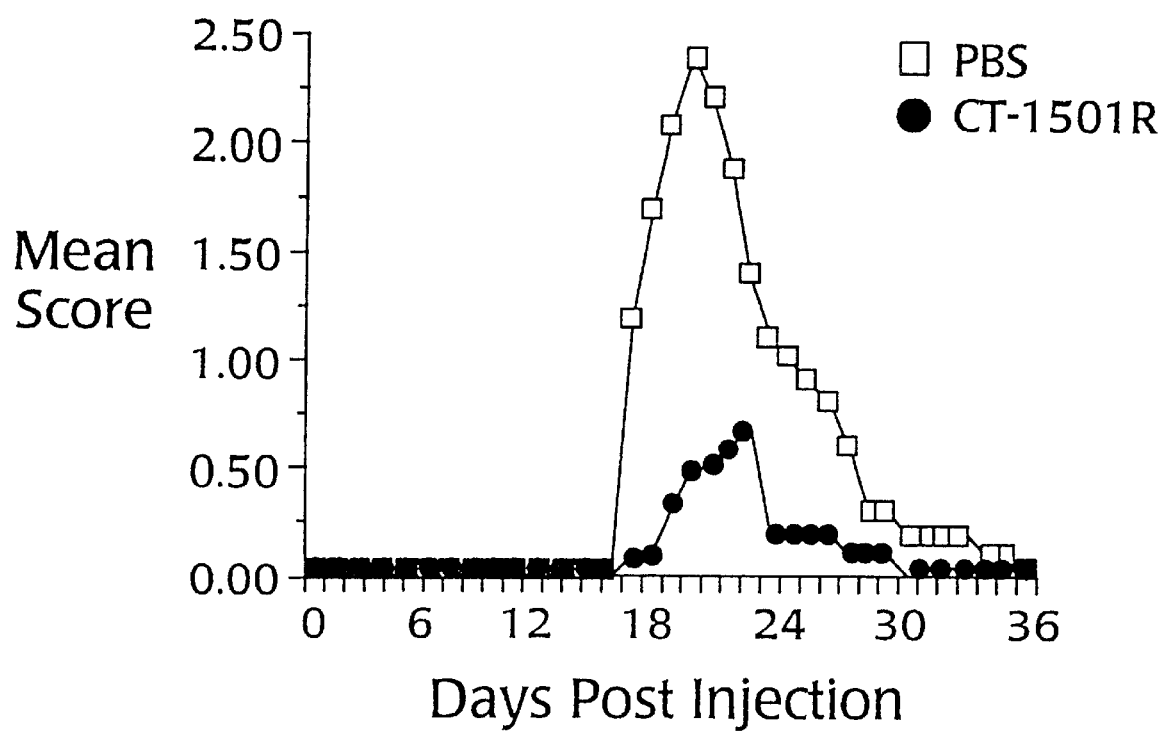
FIG. 1 shows the ability of (R)-1-(5-hydroxyhexyl)-3,7-dimethylxanthine ("CT 1501R") to prevent of the induction of active EAE after MSCH immunization.

The present invention is directed to a method of inhibiting IL-12 signaling in a mammal having a CD4+ Th1 cell-mediated inflammatory response by administering a signal inhibiting amount of the compound of the following formula:

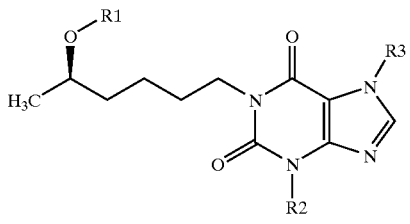

wherein, $R_1$ is H, $CH_3$, sulfate, phosphate, or salt thereof; $R_2$ is alkyl ($C_{1-12}$), alkoxyalkyl ($C_{1-11}$), dialkoxyalkyl, $CH_2C_6H_5$, —$CH_2$-ftiran, biotin; and $R_3$ is H, $CH_3$ or $CH_2C_6H_5$.

The methods of the present invention employ compounds characterized by their ability to inhibit IL-12 signaling. Inhibition of IL-12 signaling decreases the production of IFN-γ, thus mitigating the inflammatory response in disease conditions mediated by CD4+ Th1 cells. Specifically, the present invention impedes signaling that induces differentiation of T cells to Th1 cells. In general, differentiated Th1 cells produce high levels of IFN-γ, which incites inflammation, a component of many disease conditions that the inventive methods target.

The methods of the present invention generally comprise administering a therapeutically effective amount of a compound as described herein to a patient in need of such treatment. A patient will need treatment when exhibiting a deleterious inflammatory response in the course of a disease condition mediated by CD4+ Th1 cells. Such need is determinable by skilled clinicians and investigators in the medical arts. Preferred CD4+ Th1 cell-mediated disease conditions which involve an inflammatory response may include, but are not limited to, the following exemplary conditions: chronic inflammatory disease, chronic intestinal inflammation, arthritis, psoriasis, asthma, and autoimmune disorders. Autoimmune disorders, include multiple sclerosis, type-1 insulin dependent diabetes mellitus, rheumatoid arthritis, lupus disorders, acute graft-versus-host disease, autoimmune thyroid diseases, such as Graves' Disease and Hashimoto's Disease, and inflammatory bowel diseases, such as Crohn's Disease and ulcerative colitis. The patient may be a human or non-human mammal.

The method of the present invention is particularly useful in the treatment of autoimmune diseases, preferably as a therapy for treating MS and type-1-insulin dependent diabetes mellitus.

The inventive methods employ variously substituted xanthine compounds having the ability to inhibit IL-12 signaling. In more preferred methods, administered compounds have the following formula:

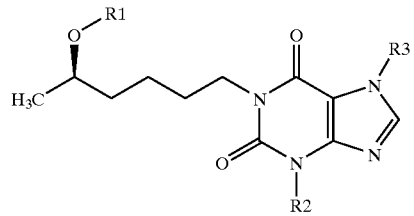

wherein the $R_1$ substituent is independently selected from the group consisting of H, $CH_3$, sulfate, phosphate, or salt. Other preferred compounds of the present invention have $R_1$ as a sulfate or phosphate or salt thereof.

The $R_2$ substituent is independently substituted or unsubstituted alkyl ($C_{1-12}$), alkoxyalkyl ($C_{1-11}$), dialkoxyalkyl, $CH_2C_6H_5$, a —$CH_2$-furan, biotin. Preferably, the administered compounds have $R_2$ as alkyl ($C_{1-12}$), biotin, or —$CH_2$-furan. More preferably, $R_2$ is alkyl ($C_{1-12}$). In the most preferred compounds, $R_2$ is methyl.

The $R_3$ substituent is independently H, $CH_3$ or $CH_2C_6H_5$. More preferably, $R_3$ is H or methyl. In the most preferred compounds, $R_3$ is methyl.

The preferred compounds administered in the inventive method are compounds in which $R_1$ is H, $CH_3$, sulfate, phosphate, or a salt thereof, $R_2$ is independently substituted or unsubstituted alkyl ($C_{1-12}$), alkoxyalkyl ($C_{1-11}$), dialkoxyalkyl, $CH_2C_6H_5$, $CH_2$-furan, biotin and $R_3$ is methyl. More preferably, compounds administered in the inventive method are compounds in which $R_1$ is H, $CH_3$, sulfate, phosphate, or a salt thereof, $R_2$ is substituted or unsubstituted alkyl ($C_{1-12}$), and $R_3$ is methyl. The most preferred compounds are those compounds in which $R_2$ and $R_3$ are both methyl. Species illustrating preferred compounds within the scope of the inventive method, include, without limitation: (R)-1-(5-Hydroxyhexyl)-3,7-dimethylxanthine 5'-sulfate, sodium salt, and (R)-1-(5-Hydroxyhexyl)-3,7-dimethylxanthine 5'-phosphate (R)-3-(6-Biotinylamidohexyl)-1-(5-hydroxyhexyl)-7-methylxanthine and (R)-1-(5-hydroxyhexyl)-3,7-dimethylxanthine. Representative compounds according to the present invention may include:

Ct-2460R

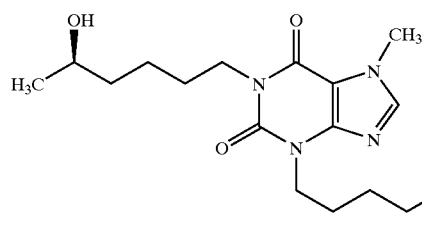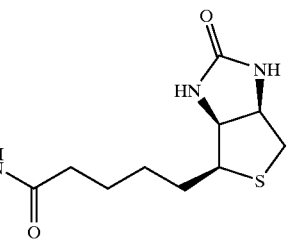

-continued
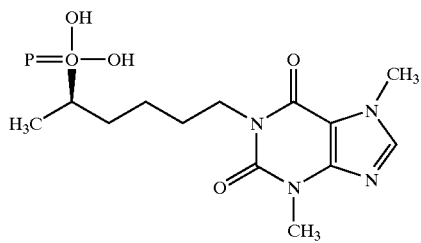
Ct-7557R
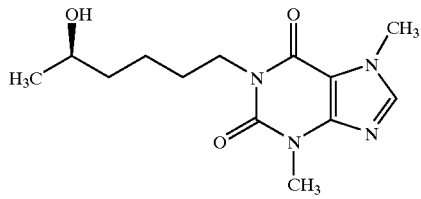
Ct-1501R
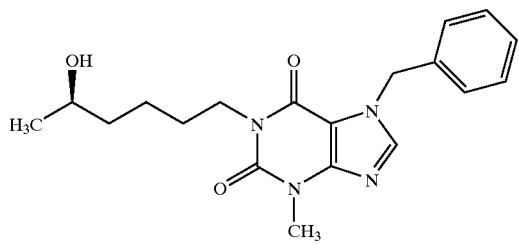
Ct-2404S
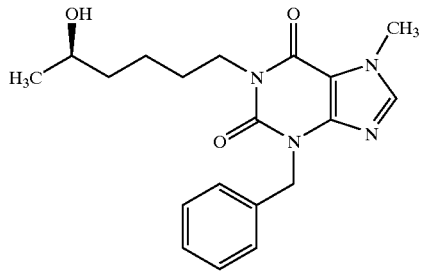
Ct-2421R
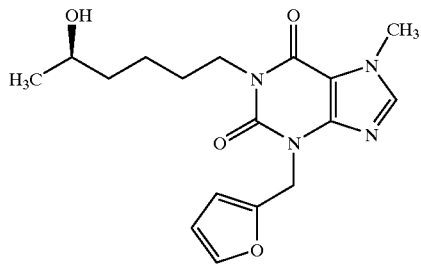
Ct-2422R
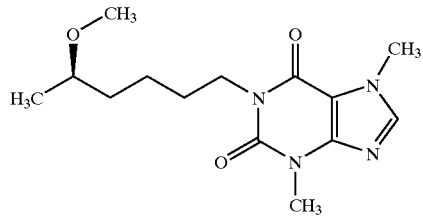
Ct-1570R

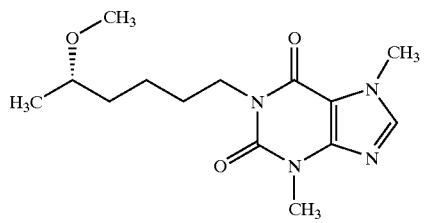

Ct-1570S

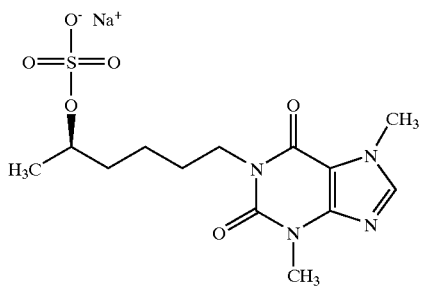

Ct-7556R

Other compounds that may be employed in the methods of the present invention are described, for example, in copending U.S. Ser. Nos. 08/932,834, and 08/472,296.

In addition to their structural characteristics, the compounds of the present invention share an ability to inhibit IL-12 signaling. A scientist using routine assays may readily confirm the inhibition of the compounds. An example of one such assay is the Th1 differentiation assay, which is included in Comparative Example 1.

The inventive methods are for administering pharmaceutical compositions, which generally contain a therapeutically effective amount of one or more of the foregoing compounds, or their pharmaceutically acceptable salts. Pharmaceutically acceptable salts will be readily apparent to the skilled clinician. Preferably, these one or more compounds, or their pharmaceutically acceptable salts, are admixed with a pharmaceutically acceptable excipient. The pharmaceutical formulations can contain isolated R- or S-enantiomers or racemic mixtures of these compounds.

A suitable formulation will depend on the nature of the disorder to be treated, the nature of the medicament chosen, and the judgment of the attending physician. In general, the compounds are formulated either for oral administration or injection, although other modes of administration such as transmucosal or transdermal routes may be employed. Suitable formulations for these compounds, including pharmaceutically acceptable excipients, can be found, for example, in *Remington's Pharmaceutical Sciences,* Chapters 83–92, pages 1519–1714 (Mack Publishing Company 1990) (Remington's), which is hereby incorporated by reference.

The compounds and their pharmaceutically acceptable salts can be employed in a wide variety of pharmaceutical forms. The preparation of pharmaceutically acceptable salts is largely determined by the chemical nature of the compound itself, and can be prepared by conventional techniques readily available.

Thus, if a solid carrier is used then the preparation can be tableted, placed in a hard gelatin capsule in powder or pellet form or in the form of a troche or lozenge. The amount of solid carrier will vary widely but preferably will be from about 25 mg to about 1 gram.

Where the composition is in the form of a capsule, any routine encapsulation is suitable, for example, using the aforementioned carriers in a hard gelatin capsule shell.

Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell.

When a liquid carrier is used, the preparation may be in the form of a syrup, emulsion, soft gelatin capsule, sterile injectable liquid such as an ampule or nonaqueous liquid suspension.

A syrup formulation will generally consist of a suspension or solution of the compound or salt thereof in a liquid carrier with a flavor or coloring agent. Examples of liquid carriers include ethanol, polyethylene glycol, coconut oil, glycerine and water.

Although other routes of administration are contemplated, the pharmaceutical compositions of the invention preferably are suitable for oral, intravenous, intraperitoneal, intramuscular, subcutaneous, parenteral, ex vivo culture, or topical delivery. Preferred administration is accomplished orally.

Parenteral administration can include intravenous ("i.v."), intramuscular ("i.m."), subcutaneous ("s.c."), intranasal, intrarectal, intravaginal or intraperitoneal ("i.p.") administration.

Additionally, the compounds may be administered by, for example, intranasal or oral inhalation. Appropriate dosage forms for inhalation include an aerosol or a metered dose inhaler, as prepared by conventional techniques. Typical compounds for inhalation are in the form of a solution, suspension or emulsion that may be administered as a dry powder or in the form of an aerosol using a conventional propellant.

Appropriate dosage forms for each specific route of administration may be prepared by conventional techniques. A typical dosage form for parenteral administration is a solution or suspension of at least one inventive compound, or its pharmaceutically acceptable salt. The parenteral dosage form typically contains a parenterally acceptable sterile aqueous or non-aqueous carrier. The parenteral dosage form optionally contains a parenterally acceptable oil. Examples of such oils include polyethylene glycol, polyvinylpyrrolidone, lecithin, arachis oil, and sesame oil. Parenteral acceptability is known to the skilled clinician.

Formulation as a standard unit dose also is contemplated. Thus, the pharmaceutical compositions of the invention can be formulated, for example, for oral use in dosage unit form as a pill, a tablet, a caplet, or a capsule. These dosage units may each contain a therapeutically effective amount of one or more compounds of the invention. These dosage units also may contain subtherapeutically effective amounts, where multiple units may be combined to achieve a therapeutically effective amount. The amount of compound in a unit dose will depend on many factors considered by the skilled clinician. Generally, however, dosage units prepared for oral use will contain from about 5 mg to about 5000 mg of compound of the invention. Preferred oral formulations contain from about 100 mg to about 2500 mg of compound, whereas other preferred formulations contain from about 500 mg to about 1500 mg. Such formulation conveniently can be administered one to six, and preferably, two or three times daily.

A typical parenteral unit does can be from about 1 g to about 5 g and may be administered (i.v., i.p., i.m., or s.c.) over a course of 24 hours. A typical topical formulation contains from about 1% to about 4% by weight. An ex vivo culture concentration can be maintained from about 10 $\mu$M to about 500 $\mu$M.

The invention is further described by the presentation of the following examples, offered by way of illustration and not by limitation.

EXAMPLE 1

(R)-3-(6-Biotinylamidohexyl)-1-(5-hydroxyhexyl)-7-methylxanthine
(CT 2460R)

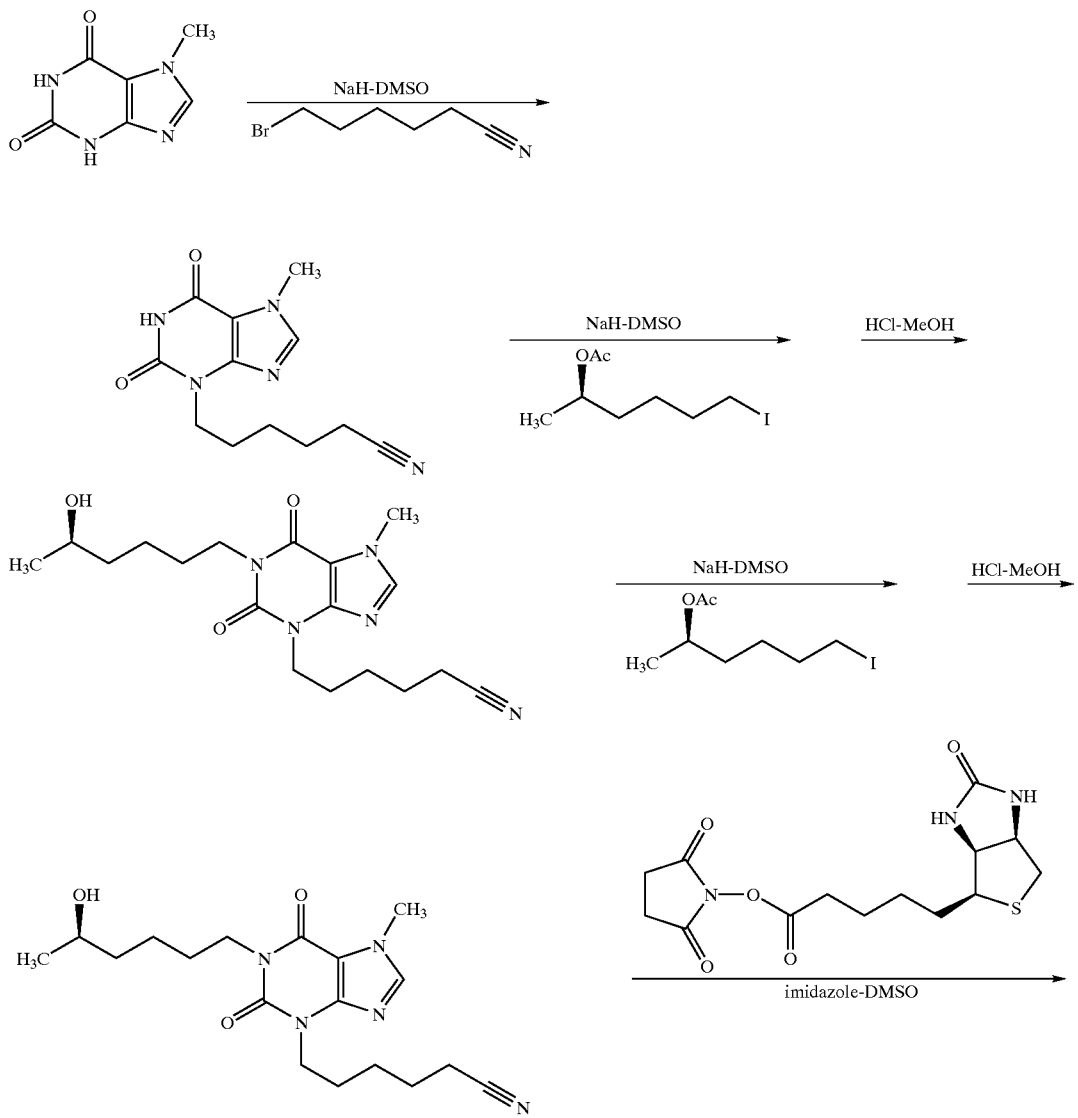

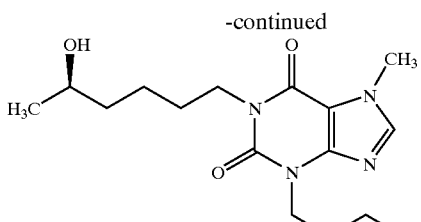
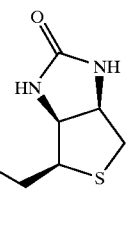

To a stirring slurry of 2.69 g 7-methylxanthine (16.2 mmol) (Aldrich, Milwaukee, Wis.) in 50 ml methyl sulfoxide was added 0.39 g sodium hydride (16.2 mmol). After 1 hour, 2.85 g of 6-bromocapronitrile (16.2 mmol) (Lancaster Synthesis, Inc., Windham, N.H.) was added neat and the reaction was stirred for 72 h at room temperature. The mixture was then quenched with 150 mL water and extracted five times with 35 ml methyl acetate. The combined extracts were washed two times with 40 ml saturated aqueous sodium bicarbonate solution and two times with 40 ml saturated aqueous sodium chloride solution and then dried over sodium sulfate. After concentration under vacuum, the residual white powder was recrystallized with ethyl acetate-hexane solution to yield 0.64 g 3-(cyanopentyl)-7-methylxanthine (15% yield) as a white solid.

A solution of 4.80 g (R)-5-acetoxy-1-chlorohexane (26.89 mmol) (prepared in accordance with procedures set forth in U.S. Pat. No. 5,629,423) was added to 5.39 g sodium iodide (36 mmol) in a round bottomed flask fitted with magnetic stirrer bar and a reflux condenser and refluxed for 12 h with stirring. Acetone was removed under reduced pressure. The crude product was partitioned between 60 ml ethyl acetate and 60 ml water layer. The organic layer was washed with 10% sodium thiosulphate solution followed by 20 ml water and then dried over anhydrous magnesium sulfate and concentrated under reduced pressure to yield 7 g (96%) (R)-5-Acetoxy-1-iodohexane.

To a stirring solution of 0.31 g 3-(cyanopentyl)-7-methylxanthine (1.2 mmol) in 20 ml dimethyl sulfoxide was added 30 mg sodium hydride (1.3 mmol). After 25 minutes, 0.34 g of (R)-5-acetoxy-1-iodohexane (1.3 mol) was added and the mixture was stirred for 24 h. The mixture was then quenched with 70 ml water and extracted three times with 30 ml ethyl acetate. The combined extracts were washed two times with 35 ml saturated aqueous sodium chloride solution and dried over sodium sulfate, and concentrated under vacuum. The residue was purified by flash chromatography (silica gel) eluting with 5% methanol-ethyl acetate to give 0.42 g (R)-1-(5-acetoxyhexyl)-3-(5-cyanopentyl)-7-methylxanthine (88% yield) as a viscous oil.

To a stirring solution of 0.37 g (R)-1-(5-acetoxyhexyl)-3-(5-cyanopentyl)-7-methylxanthine (0.92 mmol) in 20 ml methanol was added a solution of 4M hydrogen chloride in 70 ml 1,4-dioxane (2.77 mmol). The reaction was heated at reflux (80° C.) for five hours and then cooled to room temperature. The solvent was removed under reduced pressure and the resulting oil was treated with 25 ml saturated aqueous sodium bicarbonate solution and extracted three times with 25 ml dichloromethane. The combined extracts were washed 2x with 25 ml saturated aqueous sodium chloride solution dried over sodium sulfate, and concentrated under vacuum. The resulting residue was purified by flash chromatography eluting with 10% methanol-ethyl acetate to give 0.15 g (R)-3-(5-cyanopentyl)-1-(5-hydroxyhexyl)-7-methylxanthine (47% yield) as a viscous oil.

A slurry of 0.14 g (R)-3-(5-cyanopentyl)-1-(5-hydroxyhexyl)-7-methylxanthine (0.39 mmol), 15 mg 10% Palladium on carbon, seven drops hydrochloric acid, and 35 ml absolute ethanol was treated with 70 psi hydrogen gas on a Parr shaker for 4 h. After filtration through a pad of celite, the solution was concentrated under vacuum to give 84 mg (R)-3-(6-aminohexyl)-1-(5-hydroxyhexyl)-7-methylxanthine hydrochloride (54% yield).

A solution of 24 mg (R)-3-(6-aminohexyl)-1-(5-hydroxyhexyl)-7-methylxanthine hydrochloride (0.07 mmol), 27 mg biotin N-hydroxysuccinimide ester (0.08 mmol) (CalBiochem, San Diego, Calif.), and nine mg imidazole (0.13 mmol) in 1 ml dimethyl sulfoxide was stirred for six h. The solution was treated with 10 ml saturated aqueous sodium chloride solution and extracted two times with 15 ml dichloromethane. The combined extracts were dried over magnesium sulfate and concentrated under vacuum. The residue was purified by flash chromatography (silica gel) eluting with 7% methanol-ethyl acetate followed by 100% methanol to provide (R)-3-(6-Biotinylamidohexyl)-1-(5-hydroxyhexyl)-7-methylxanthine. The compound was further purified by treating with 10 ml of 1.5 M aqueous hydrochloric acid and extracting with 30 ml ethyl acetate. The aqueous layer was neutralized by the addition of 25 ml saturated aqueous sodium bicarbonate solution and saturated with solid sodium chloride, and extracted three times with 15 ml 20% methanol-dichloromethane. The combined extracts were dried over magnesium sulfate and concentrated under vacuum to give 7 mg (R)-3-(6-Biotinylamidohexyl)-1-(5-hydroxyhexyl)-7-methylxanthine (18% yield).

EXAMPLE 2

Procedure for the synthesis of
(R)-1-(5-Hydroxyhexyl)-3,7-dimethylxanthine 5'-sulfate, sodium salt
(CT 7556R)

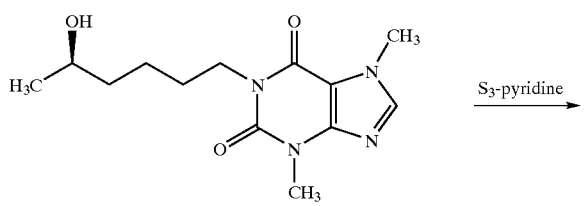

-continued

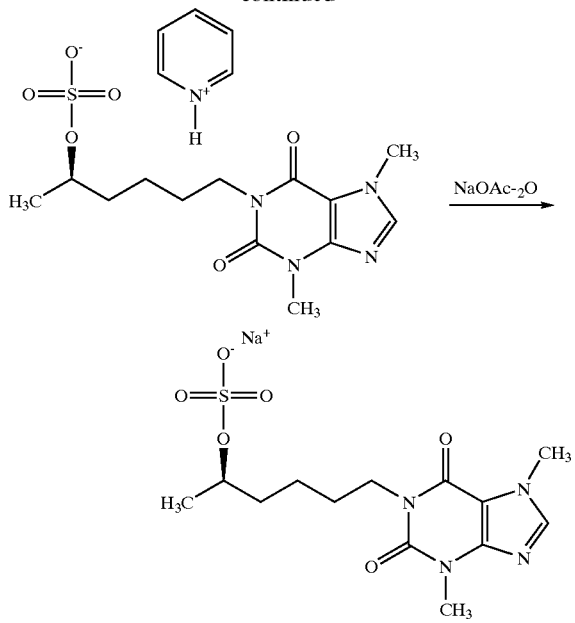

To a 25 ml round bottomed flask was added 300 mg of (R)-1-(5-hydroxyhexyl)-3,7-dimethylxanthine 250 mg, (1.07 mmol) and 6mL pyridine, prepared in accordance with procedures set forth in Bianco et al., U.S. Pat. No. 5,648, 357, for example). Then 375 mg of sulfur trioxide pyridine complex (2.36 mmol) was added and the resulting mixture was stirred for 18 h at room temperature. The resulting solution was concentrated under vacuum to remove most of the pyridine. The residue was then diluted in 10 ml of methanol and 10 ml 0.2M sodium hydroxide-methanol was added to the solution. The mixture was filtered and the resulting solid was washed two times with 10 ml with methanol. The combined filtrates were concentrated under vacuum. To the residue was added 5 ml of a 0.2M aqueous sodium acetate solution and The mixture was stirred at room temperature until homogeneous. The mixture was then concentrated under vacuum to remove water yielded 410 mg (R)-1-(5-Hydroxyhexyl)-3,7-dimethylxanthine 5'-sulfate, sodium salt as a clear viscous oil.

EXAMPLE 3

Procedure for the Synthesis of (S)-1-(5-Hydroxyhexyl)-3,7-dimethylxanthine 5'-sulfate, Sodium Salt(CT 7556S)

To a 25 ml round bottomed flask 250 mg (S)-1-(5-Hydroxyhexyl)-3,7-dimethylxanthine (0.9 mmol) (prepared in accordance with procedures set forth in Bianco et al., U.S. Pat. No. 5,648,352), six ml pyridine, and 375 mg sulfur trioxide pyridine complex (2.36 mmol) was added and stirred for 18 h. The solution was concentrated under vacuum to remove most of the pyridine. The resulting residue was added to 10 ml methanol and 10 ml 0.2M sodium hydroxide-methanol solution. The mixture was then filtered and the solid was washed twice with 10 ml methanol. The combined filtrates were then concentrated under vacuum. To the concentrated filtrates was added 5 ml of a 0.2M aqueous sodium acetate solution and the mixture was stirred until homogeneous. The resulting residue was concentrated under vacuum to remove water to yield 410 mg (S)-1-(5-Hydroxyhexyl)-3,7-dimethylxanthine 5'-sulfate, sodium salt (CT 7556S) (1.07 mmol) as a clear viscous oil.

EXAMPLE 4

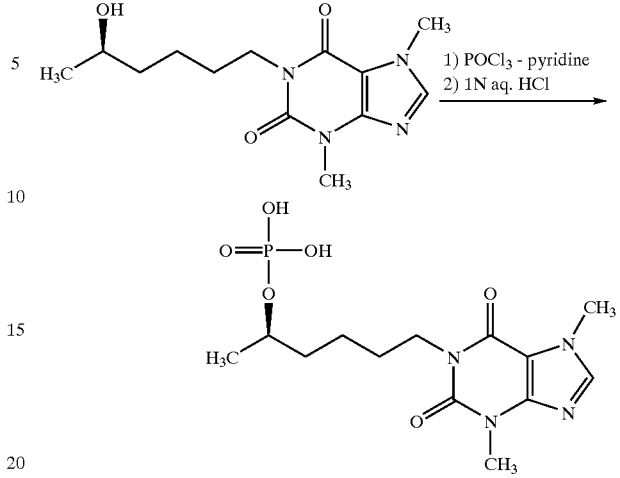

To a 25 ml round bottomed flask 303 mg of (R)-1-(5-Hydroxyhexyl)-3,7-dimethylxanthine (1.1 mmol) and 5 ml pyridine were added. The mixture was cooled in an ice bath and 200 µL of phosphorus oxychloride (2.2 mmol) (Aldrich, Milwaukee, Wis.) was added. After 2 min in the cooling bath, the mixture was removed and stirred for an additional 5 min. The solution was then concentrated under vacuum and 10 ml 1N aqueous hydrochloric acid solution was added. The white solid residue was purified by flash chromatography, (26 g of silica gel) eluting with 200 ml of a 20% methanol-ethyl acetate solution, after concentrating under vacuum, to remove the water. The yield was 70 mg (R)-1-(5-Hydroxyhexyl)-3,7-dimethylxanthine 5'-phosphate (0.19 mmol) as a clear viscous oil which solidified.

EXAMPLE 5

CT 1501R Inhibits Induction of Active and Passive Experimental Autoimmune Encephalomyelitis ("EAE")

Example 5 illustrates the effect of CT 1501R on decreasing the severity of paralysis in both active and passive models of murine EAE.

a) Active EAE

Active EAE was induced by immunization of female SJL/J mice (Clarence Reader (NIH, Bethesda, Md.)) with 800 µg of mouse spinal cord homogenate ("MSCH") in complete Freund's adjuvant ("CFA") on days zero and seven; following the procedure described in Racke et al., *J. Neuroimmunol.*, Vol 46:175–184, (1993). The mice were treated with either CT 1501R ("CT 1501R") (1 mg per dose, i.e. 50 mg/kg) or PBS by gavage twice daily for 15 days.

b) Passive EAE

Passive EAE was induced by adoptive transfer of myelin basic protein ("MBP")-sensitized T lymphocytes as follows: female SJL/J mice (four- to six-weeks-old) were immunized on days zero and seven with 400 µg of MBP in CFA. On day 14 the regional draining lymph node cells and spleen were harvested and cultured. The cells were cultured at $4 \times 10^6$ cells/well in RPMI 1640 (Gibco, Gaithersburg, Md.) containing 10% fetal bovine serum (Hyclone Labs, Logan, Utah), 2 mM L-glutamine (Gibco, Gaithersburg, Md.), five times $10^{-5}$ M 2-mercaptoethanol (Gibco, Gaithersburg, Md.), 1% penicillin/streptomycin (Gibco, Gaithersburg, Md.), and 100 μg/ml of MBP. After four days, viable T cell blasts were harvested, washed twice in PBS, and injected intraperitoneally into recipient mice ($1.0 \times 10^7$ to $1.5 \times 10^7$ cells in 500 μl of PBS).

As stated above, mice were administered either CT 1501R or PBS twice daily by gavage needle in volumes of 0.25 or 0.5 ml/dose for 6 days. At the time of disease onset, paralysis was scored according to the following clinical conditions:

0, no paralysis; 0.5, stiff tail; 1, limp tail; 1.5, limp tail with inability to right; 2, paralysis of one limb; 2.5, paralysis of one limb and weakness of one other limb; 3, complete paralysis of both hind limbs; 4, moribund state; and 5, death.

To assess the degree of inflammation, mice were euthanized on day 25 and perfused by intracardiac injection of 4% paraformaldehyde (Gibco, Gaithersburg, Md.) and 1% glutaraldehyde (Gibco, Gaithersburg, Md.) in PBS. Transverse sections of the cervical, upper thoracic, lower thoracic and lumbar region of the spinal cord were stained with luxol fast blue (Sigma, St. Louis, Mo.) or with hematoxylin blue (Sigma, St. Louis, Mo.) and eosin blue (Sigma, St. Louis, Mo.). Each spinal cord section was further subdivided into an anterior, posterior and two lateral columns. To determine the degree of inflammation, the stained spinal cord sections were viewed to determine lymphocyte infiltration and demyelination, with any subsection displaying infiltration or demyelination receiving a score of one. Therefore, each animal had a potential maximum score of 16. Spinal cords were isolated from PBS- or CT 1501R-treated mice on day 25, following induction of passive EAE by adoptive transfer of MBP-specific T cells. Demyelination and infiltration were scored in 3 mice per group (FIG. 3).

1. Active EAE

CT 1501R prevented the development of active EAE induced by MSCH immunization. The average mean clinical scores from two independent experiments for female SJL/J mice treated by gavage with 0.5 ml PBS (n=10) or CT 1501R (1.0 mg n=13) (n represents the number of mice) twice daily is represented in FIG. 1. In the control groups, seven out of 10 animals receiving PBS developed hind limb paralysis, with a mean clinical score of 2.4 on day 20. In contrast, two of 13 animals receiving CT 1501R developed paralysis with a mean clinical score of 0.75 (p<0.025). No significant difference in the day of onset of paralysis was seen.

2. Passive EAE

Figure 2:
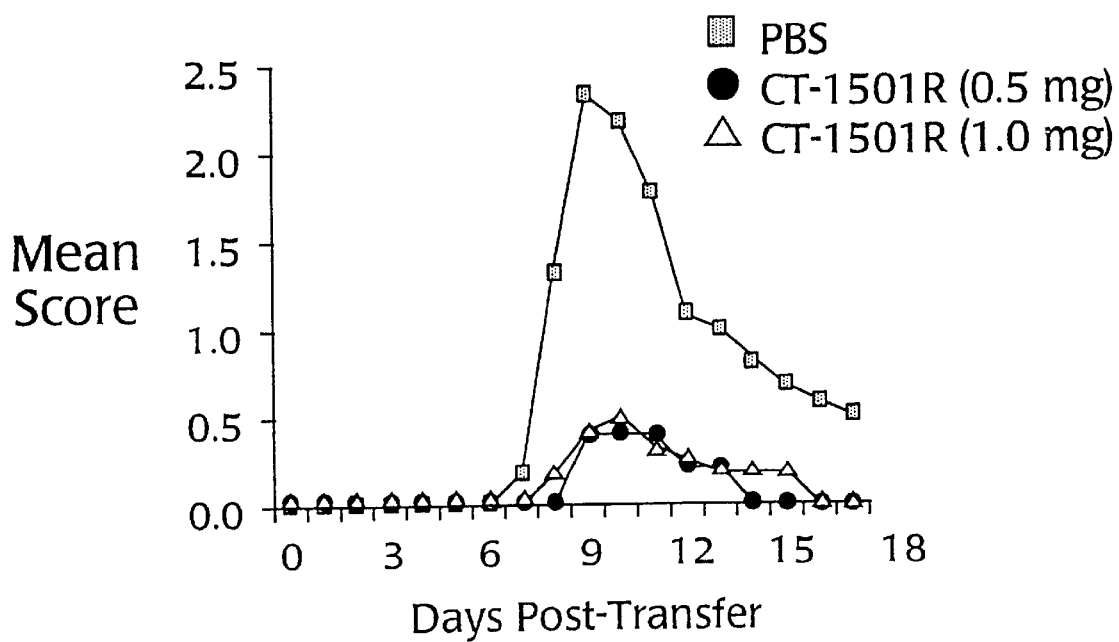
FIG. 2 shows the ability of CT 1501R to prevent the induction of passive EAE after adoptive transfer of MBP-sensitized T cells.

CT 1501R also prevented the development of passive EAE induced by adoptive transfer of MBP-sensitized T cells. The mean clinical score is depicted in FIG. 2 for female SJL/J mice treated with either PBS, n=6, or with two different doses of CT 1501R. All six mice receiving PBS developed paralytic signs, with a mean clinical score of 2.35 on day nine (FIG. 2). The mean clinical score of paralysis is also depicted for SJL/J mice treated with CT 1501R (0.5 mg or 1.0 mg, n=6 for each dose) twice daily. Only one out of the 12 mice given CT 1501R at either dose showed signs of hind limb paralysis, with a mean clinical score of 0.5 (p<0.025) (FIG. 2).

Figure 3A:
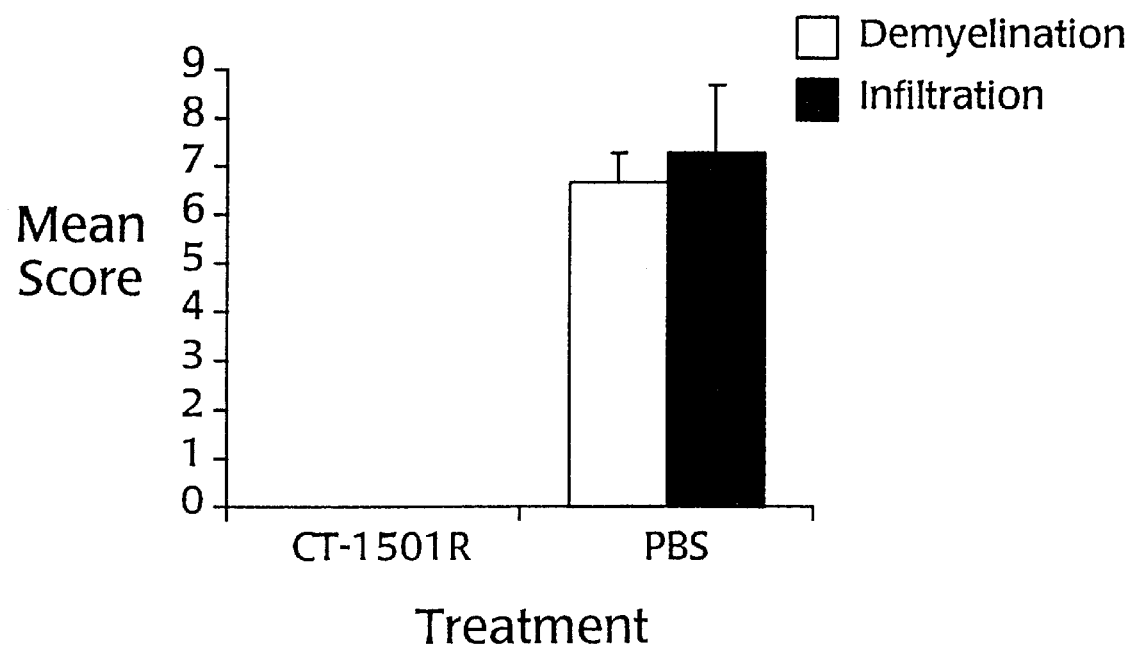

The marked differences in clinical scores for animals in the passive model were consistent with histological studies of three randomly selected animals from each group following recovery. In mice receiving PBS, the pathologic scores were 6.6 and 7.2 for demyelination and infiltration respectively, whereas no demyelination or lymphocyte infiltration into the CNS was observed in CT 1501R-treated mice (FIG. 3a and FIG. 3b). FIG. 3b, Panels A–D show the histologic sections of the spinal cord of PBS- and CT 1501R-treated mice. Panel A of FIG. 3b; shows a section of thoracic cord of a PBS-treated mouse stained with H&E. The arrow in that figure points to an area of lymphocytic infiltration. Panel B of FIG. 3b shows the same region as in Panel A but stained with LFB/PAS. This shows the lack of myelin stain (arrow). Panels C and D of FIG. 3b show comparable regions of spinal cord from a CT 1501R treated mouse. These mice showed no signs of inflammation or demyelination with CT 1501R treatment.

This example demonstrates the potent immunoregulatory properties of CT 1501R in a murine EAE model, which is felt to simulate human MS. CT 1501R inhibited the clinical manifestations of EAE induced either by immunization with MSCH or by adoptively transferred, encephalitogenic T cells (FIGS. 1 and 2). CT 1501R treated mice were protected from lymphocyte infiltration into neural tissues and demyelination, as demonstrated histologically by analysis of spinal cord sections (FIG. 3). Thus, CT 1501R blocked progression of an inflammatory, Th1 cell-mediated autoimmune disease.

EXAMPLE 6

CT 1501R Reduces in vivo Th1 Differentiation of MBP-Specific T Cells

Example 5 illustrated the ability of CT 1501R to decrease the severity of paralysis in both active and passive EAE models. This example illustrates the effects of CT 1501R in vivo on the potency and phenotype of T cells developing in MBP immunized mice.

Figure 4A:
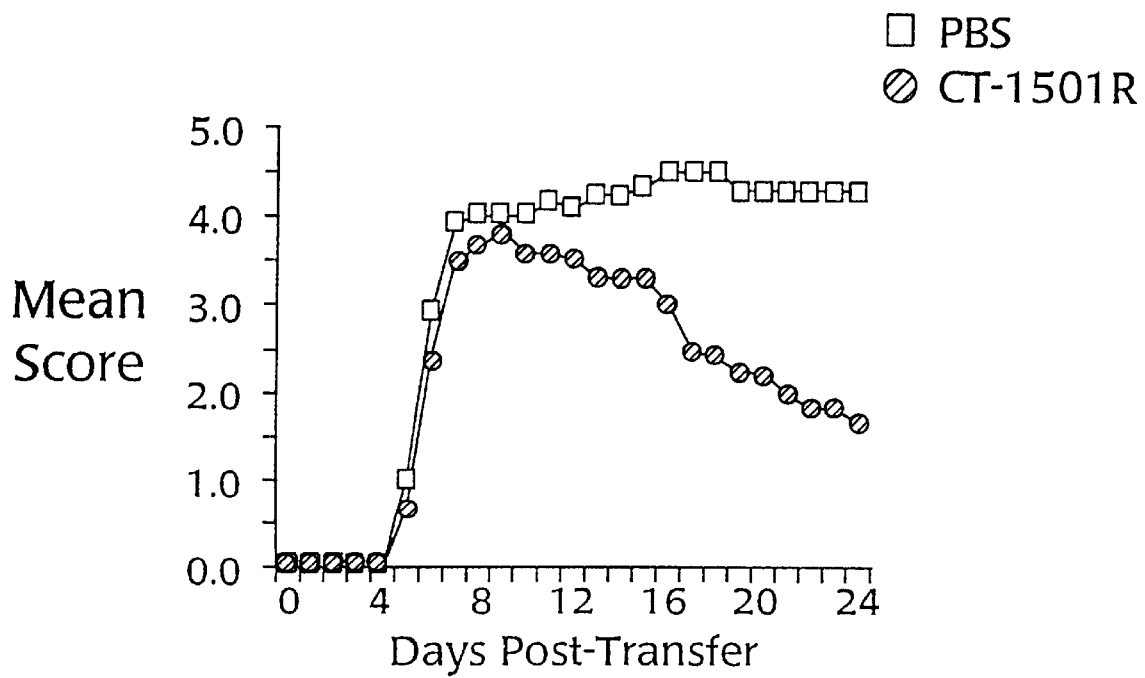
FIGS. 4a, 4b, 4c, and 4d show the ability of CT 1501R to reduce encephalitogenic potential and Th1 phenotype in donor cells, without reducing lymphocyte proliferation.

Donor SJL/J mice were treated with PBS or CT 1501R (1.0 mg twice daily) and immunized with 800 μg of MBP in CFA. The mice were immunized on day zero and boosted on day seven. LNC and spleen were harvested on day 14, cultured in the presence of 100 μg/ml of MBP for four days, and the T cell blasts (~$10 \times 10^7$) were assessed for their ability to transfer EAE to naive recipients in two separate experiments (FIGS. 4a and 4b), to proliferate in response to MBP in vitro (FIG. 4c) and to secrete IFN-γ after antigen re-stimulation in vitro (FIG. 4d).

a) Potency at Adoptively Transferring EAE

When compared to cells from PBS-treated mice, donor cells from CT 1501R-treated animals were less effective at inducing passive EAE after transfer into naive hosts. As shown in FIG. 4a, all six animals that received PBS-treated donor cells developed clinical paralysis (mean clinical score=4.5), and four died at the height of disease. In contrast, none of the mice that received cells from CT 1501R-treated mice died, their mean clinical score was 3.8, and all animals recovered to a mean clinical score of 1.8 by day 24.

Figure 4B:
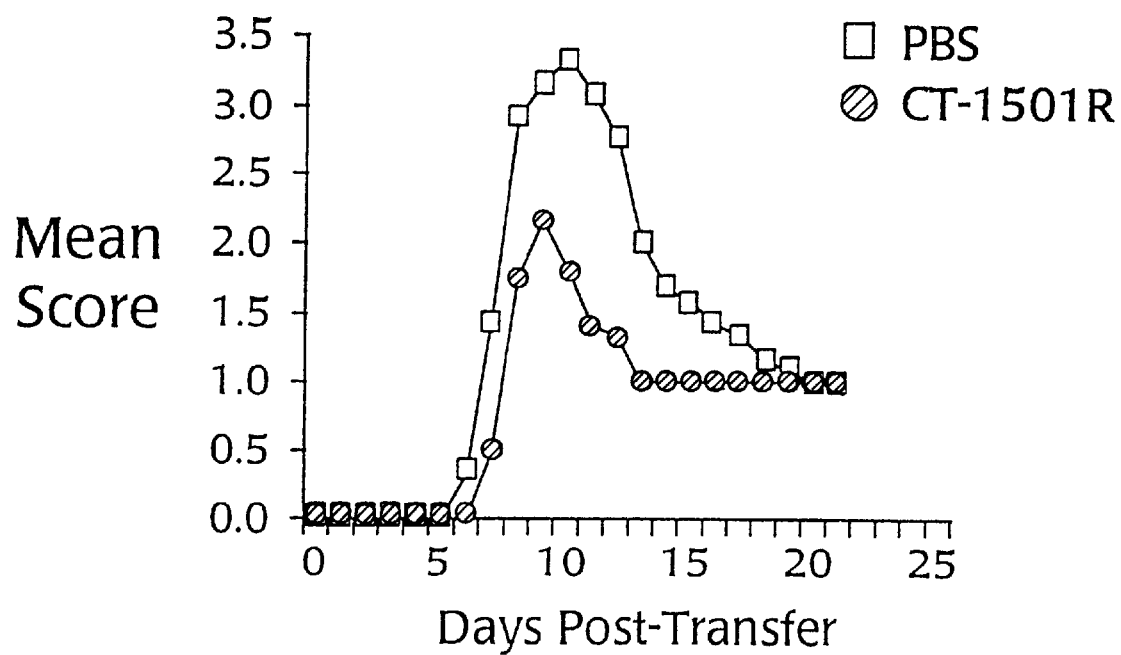

In the second experiment, the mean clinical score for mice receiving PBS treated cells was 3.25, whereas the mice receiving CT 1501R-treated cells had a mean clinical score of 2.0 (FIG. 4b).

b) Proliferative Response to MBP

The following proliferation assay was performed: 15 days after MBP immunization, PBS- or CT 1501R-treated donor cells were cultured at two times $10^5$/well with MBP for 72 h, and pulsed during The last 18 h with $^3$H-thymidine (0.5 μCi/well). $^3$H-thymidine incorporation was measured on a betaplate liquid scintillation counter (Wallac, Turku, Finland).

Figure 4C:
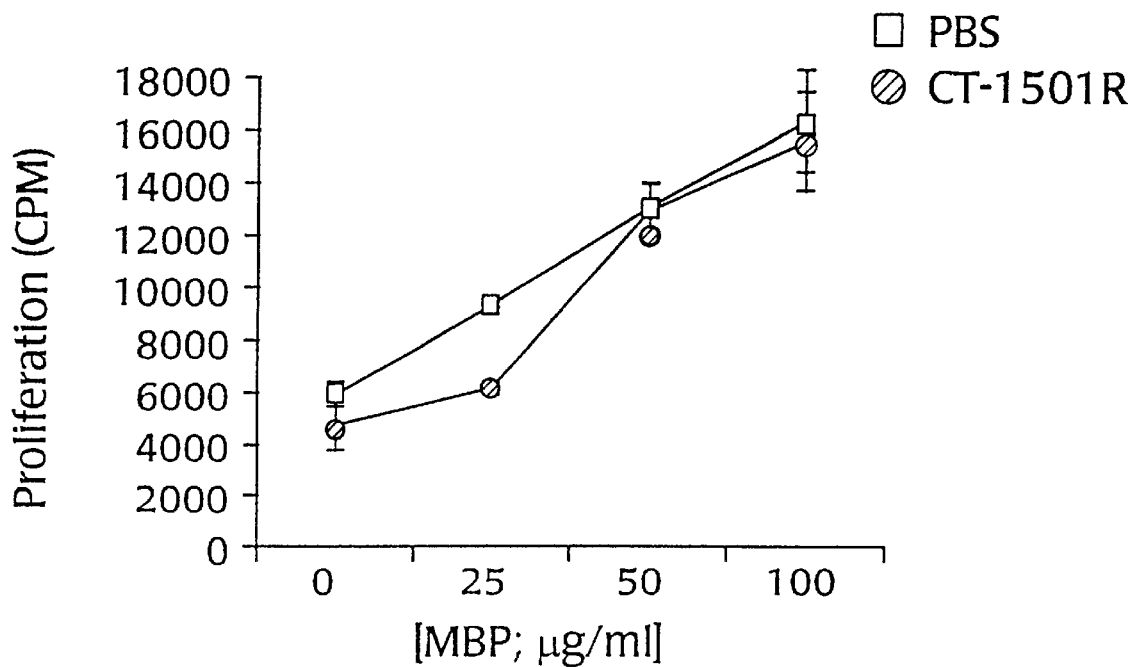
Figure 4D:
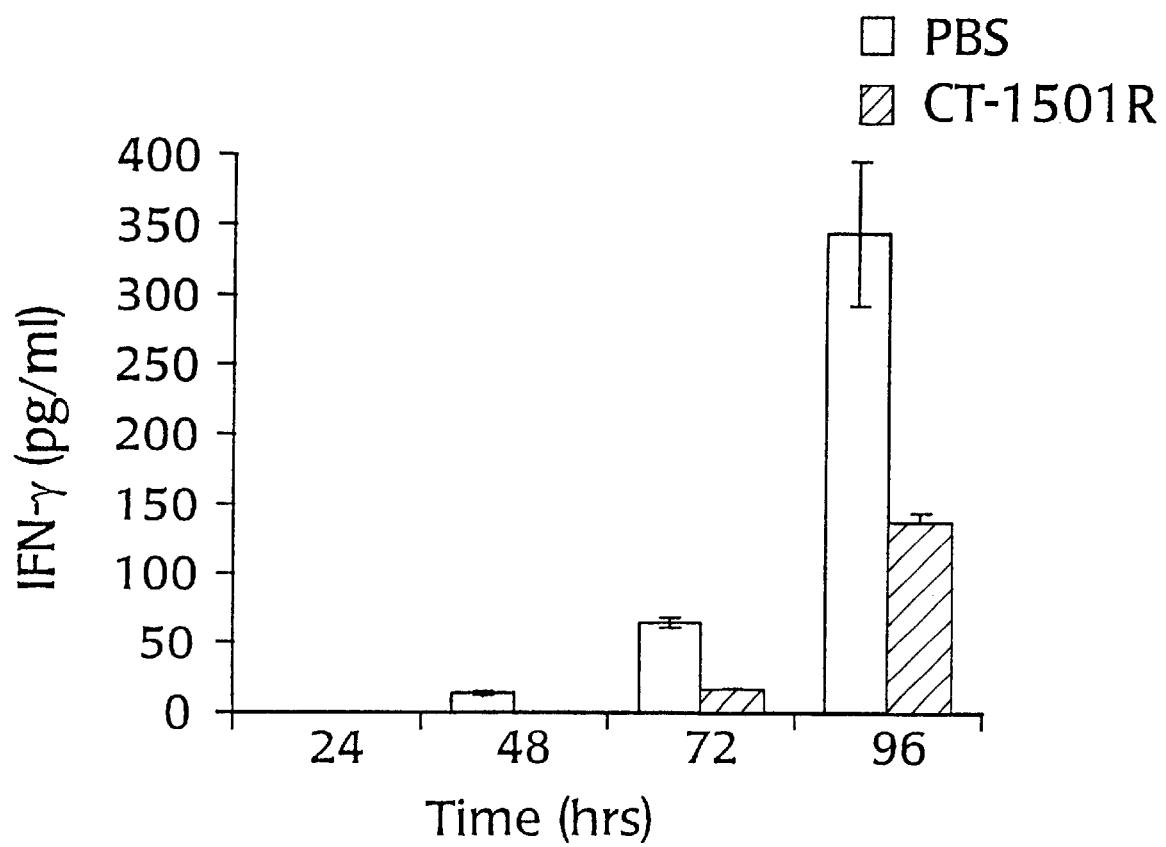

The reduction in clinical severity of EAE induced by CT 1501R-treated donor cells versus those treated with PBS-treated donor cells was significant (p<0.001), and was not due to differences in lymphocyte activation, since both populations proliferated equally well in response to MBP in vitro (FIG. 4c).

c) Capacity to Produce IFN-γ

To assess the T-helper cell phenotype of donor cells from PBS-treated and CT 1501R-treated mice supernatants from antigen-stimulated cultures were analyzed for the presence of Th1 type cytokines.

An ELISA for IL-12 secretion and IFN-γ production was performed. IL-12 secretion was determined by sandwich ELISA. Plates were coated with 2 μg/ml of anti-IL-12 antibody (C17.5 and C15.6) (gift of Dr. G. Trinchieri, Wistar Institute, Philadelphia, Pa.) and blocked with 3% bovine serum albumin in PBS. After overnight incubation at 4° C., sample wells were washed with PB S/0.05% Tween-20, and incubated with biotinylated anti-IL-12 (C17.5) at 0.2 μg/ml. After 1 h at room temperature The plates were washed, incubated for 1 h with avidin-alkaline phosphatase (Genzyme, Cambridge, Mass.), and washed again before addition of 1 mg/ml of p-nitrophenyl phosphate (Genzyme, Cambridge, Mass.). Absorbance was read at 405 nm (Biotech, Winooski, Vt.). The IL-12 concentration was calculated by interpolation from a standard curve.

IFN-γ production was also determined by the sandwich ELISA procedure, as described above, except R4-6A2 antibody (ATCC No. HB-170) was used as the capture antibody and the biotinylated anti-IFN-γ antibody, MM700, (Endogen, Woburn, Mass.) was used as the second step antibody.

In the alternative, the total IL-12 and IFN-γ levels were assayed using the commercially available Intertest-12 and the Intertest-γ ELISA kit, (Genzyme, Cambridge, Mass.). (FIG. 5 and FIG. 6).

Although no differences in IL-12 production were observed between cells from PBS-treated mice and CT 1501R-treated mice (FIG. 7), cells from CT 1501R-treated mice produced significantly less IFN-γ (FIG. 4d). CT 1501R was determined to ameliorate disease progression by examining ex vivo proliferative responses of LNC from CT 1501R-treated mice and their profiles of cytokine secretion. CT 1501R administration in vivo did not inhibit the ex vivo T cell proliferative response to MBP (FIG. 4C), indicating that CT 1501R does not induce tolerance, block antigen-specific priming, or inhibit the cellular response to subsequent antigen challenge. Furthermore, in vivo treatment with CT 1501R did not diminish IL-12 secretion by MBP-stimulated APC ex vivo implying that CT 1501R was not effective as to APC function and cytokine secretion. CT 1501R treatment reduced the amount of IFN-γ secreted by ex vivo activated T cells (FIG. 4D), implying that Th1 differentiation had been inhibited in vivo. CT 1501R inhibited Th1 differentiation by blocking IL-12 signaling and not by inhibiting IL-12 secretion from APC (FIG. 5), since IL-12-dependent Th1 differentiation was suppressed in vitro (FIG. 6). More recently, we have extended these observations to show that CT 1501R abrogates IL-12-induced proliferation of anti-CD3 activated T cell blasts (SJK, unpublished observation). The reduced capacity to produce IFN-γ correlated with a reduced capacity to adoptively transfer EAE to susceptible, naive recipients. Thus, donor cells from CT 1501R-treated animals were less encephalitogenic, which led ultimately, to lower clinical scores (FIGS. 4a and b).

EXAMPLE 7

Effect of CT 1501R on IL-12 Secretion and Signaling

This experiment demonstrates that CT 1501R inhibits IL-12 signaling in T cells but does not block IL-12 secretion from antigen-presenting cells such as macrophages, suggesting inhibition Th1 differentiation in vivo by blocking IL-12 signaling.

a) Inability of CT 1501R to Block IL-12 Secretion from APC

Figure 5A:
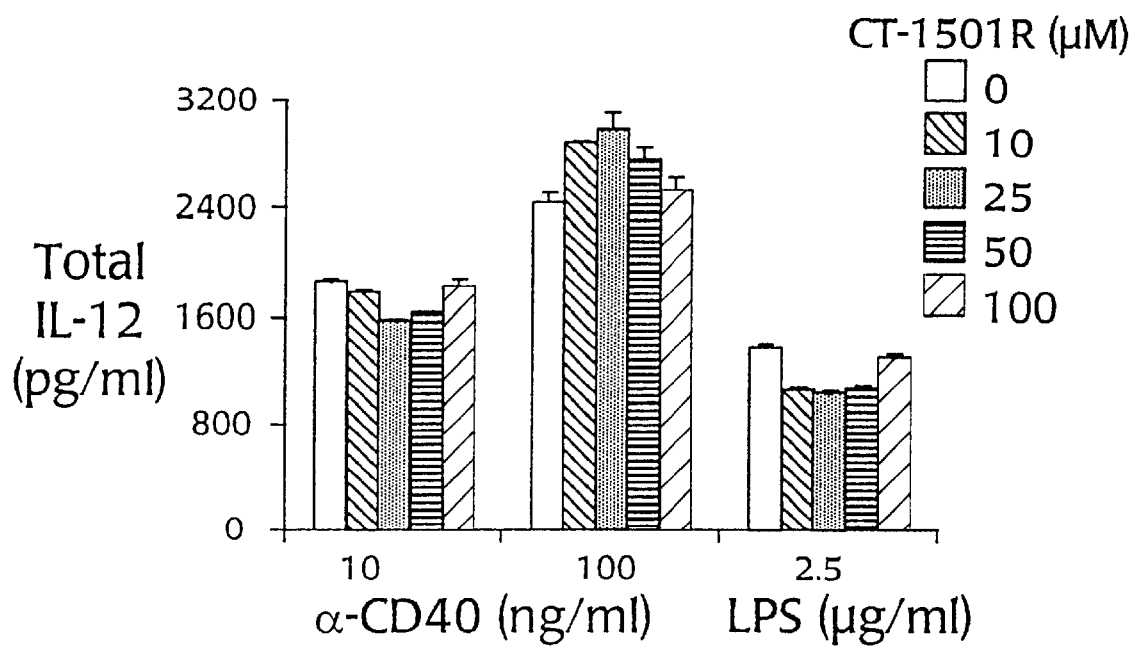
FIGS. 5a and 5b show the inability of CT 1501R to block IL-12 secretion from murine macrophage.
Figure 5B:
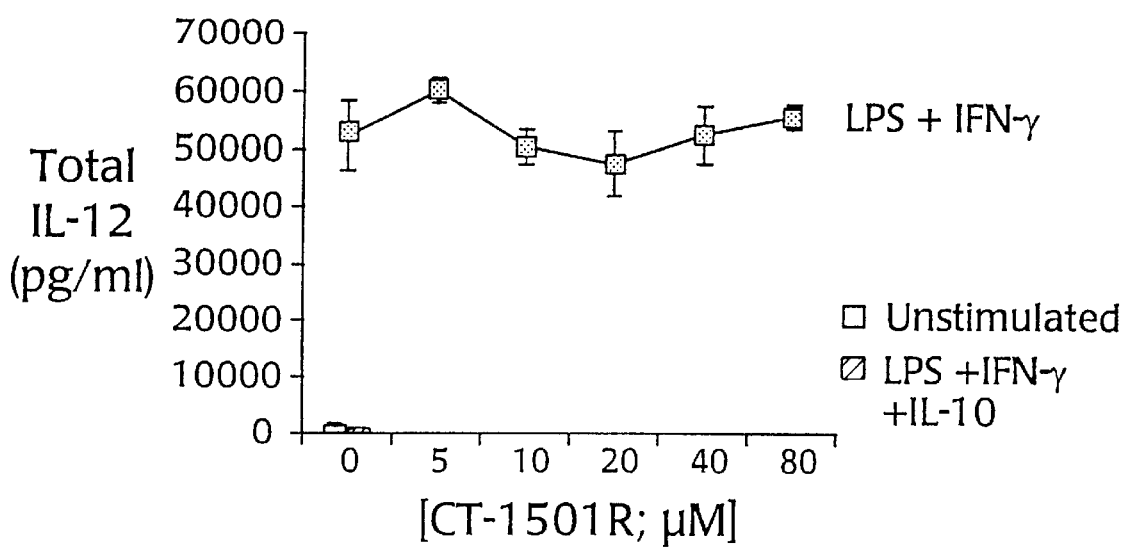

Murine macrophages were induced to secrete IL-12 after activation with anti-CD40 (HM40-3; Pharmingen, San Diego, Calif.) or LPS (Sigma, St. Louis, Mo.) (FIG. 5a). Total IL-12 production was assessed from macrophages activated in vitro in the presence of CT 1501R, using CT 1501R concentrations that were detectable in patients' sera collected during clinical trials, and up to four-fold higher.

Normal macrophages were enriched from single cell suspensions of Balb/c mice (Charles River Labs, B&K Universal, Fremont, Calif.) spleens by adherence to tissue culture plates at 37° C. for one h. Plates were rinsed four times with PBS before harvesting the adherent cells. Adherent Balb/c mice splenic cells ($10^6$/ml) were stimulated with either anti-CD40 or LPS at the indicated concentrations for 48 h in the absence or presence of increasing concentrations of CT 1501R. We also tested whether CT 1501R might inhibit IL-12 secretion from a murine macrophage cell line. The murine macrophage cell line J774A.1 (ATCC # TIB-67) ($10^6$/ml) was either left untreated, or stimulated with both one ng/ml LPS and 10 U/ml IFN-γ plus or minus increasing concentrations of CT 1501R, or plus 10 ng/ml human recombinant IL-10 (PeproTech, Rocky Hill, N.J.) without CT 1501R. Normal macrophage or The J774A.1 cell line was incubated for 48 h and the culture media collected and assayed for IL-12 by ELISA.

Normal murine macrophages were induced to secrete IL-12 after activation with anti-CD40 or LPS, but CT 1501R did not inhibit IL-12 secretion [values for IL-12 in unstimulated cultures was 68 pg/ml. (FIG. 5a)]. CT 1501R was not even inhibitory at concentrations of anti-CD40 which induce suboptimal IL-12 production. Furthermore, CT 1501R did not block IL-12 secretion from a murine macrophage line stimulated with LPS and IFN-γ (FIG. 5b), whereas recombinant human IL-10 (PeproTech, Rocky Hill, N.J.) completely abolished IL-12 secretion.

b) Ability of CT 1501R to Inhibit IL-12 Signaling in T Cells

This assay illustrates CT 1501R's ability to suppress Th1 differentiation in vitro by blocking IL-12 signaling. CT 1501R was tested in an IL-12 dependent in vitro T-helper cell differentiation assay as described in LeGross et al., *J. Exp. Med*, Vol. 172, pp. 921–929, (1990). Recombinant IL-12 was used to induce Th1 differentiation. Splenic T cells were purified utilizing The antibodies RA3-3A1/6.1 (anti-B220), J11d and MAR18.5 (anti-rat kappa chain) to deplete the B cells via complement mediated toxicity following the procedure set forth in Klaus et al. *J. Immunol.* 149:1867–1875 (1992). Splenic T cells were stimulated at five times 105/ml with insoluble anti-CD3 alone (145-2C11, Pharmingen, San Diego, Calif.), or anti-CD3 and 5 U/ml IL-12, with or without CT 1501R, at the concentrations indicated. After seven days, equal numbers of viable cells were restimulated for 24 h with anti-CD3 without CT 1501R, and the supernatants were collected and assayed for IFN-γ production. IFN-γ and IL-4 levels were measured by Intertest kits from Genzyme specific for IFN-γ and IL-4.

Figure 6A:
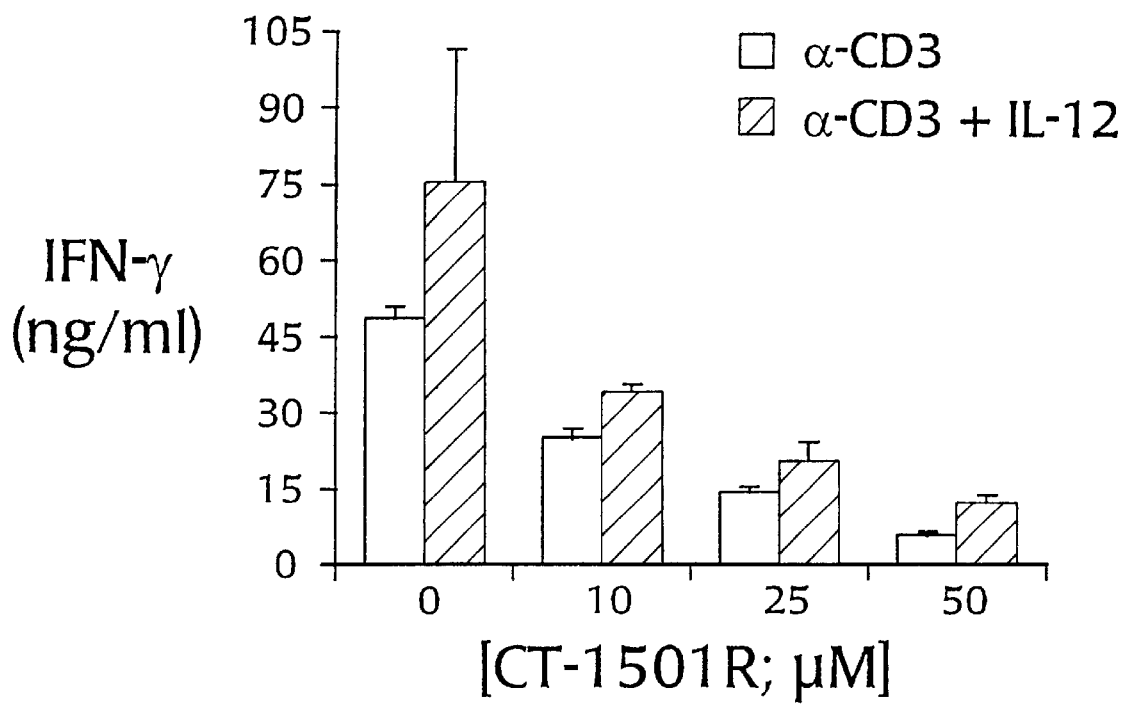
FIGS. 6a and 6b show the inability of PTX as compared with The ability of CT 1501R to reduce Th1 differentiation, in vitro.
Figure 7:
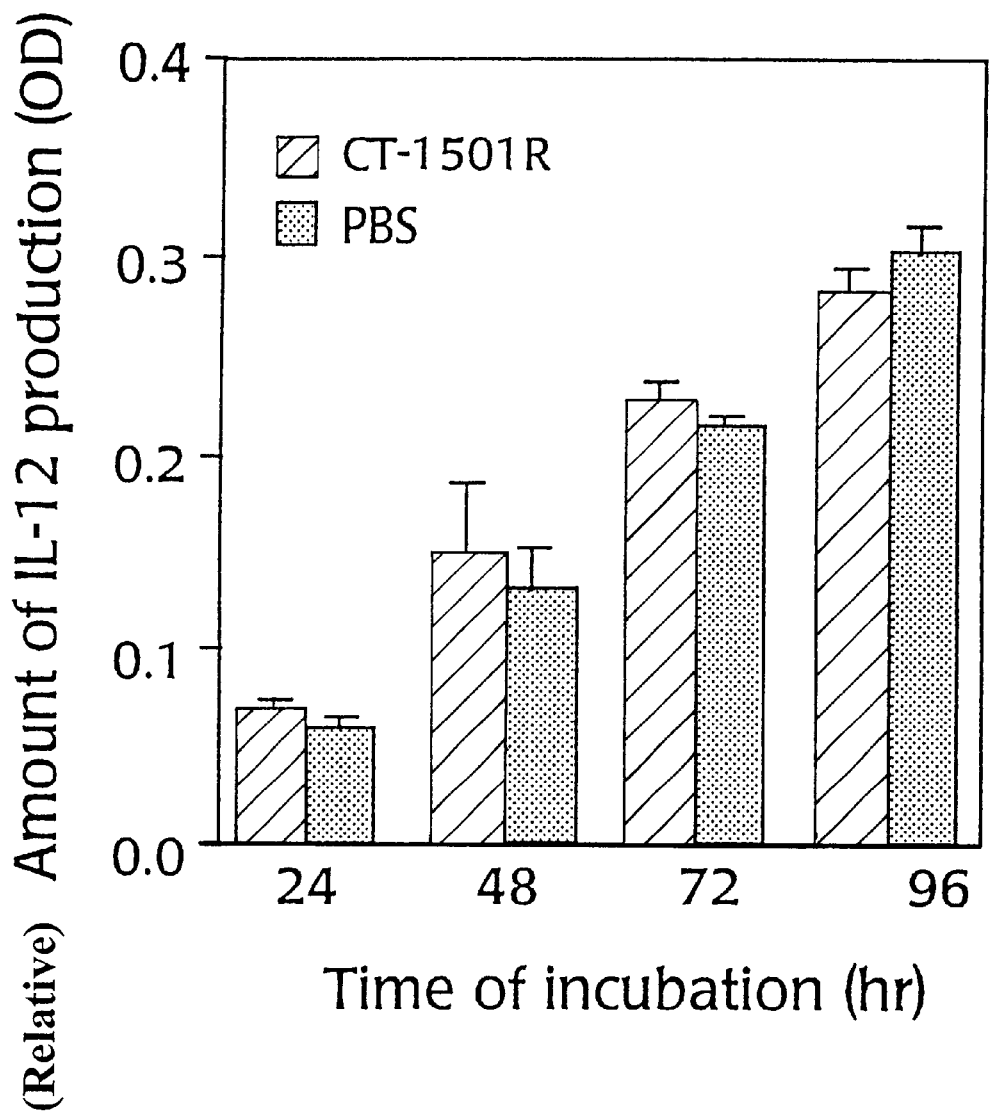
FIG. 7 shows the inability of CT 1501R to inhibit IL-12 production.
Figure 8A:
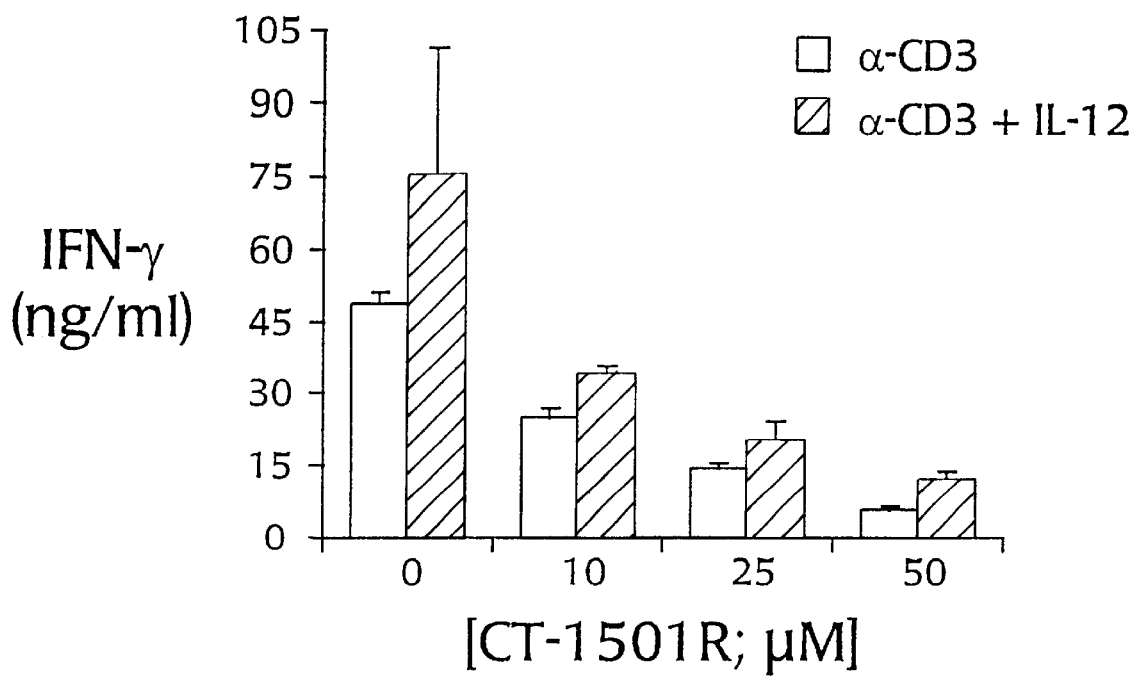
FIGS. 8a and 8b show the ability of CT 1501R to inhibit IL-12 induced Th1 cell differentiation.
Figure 8B:
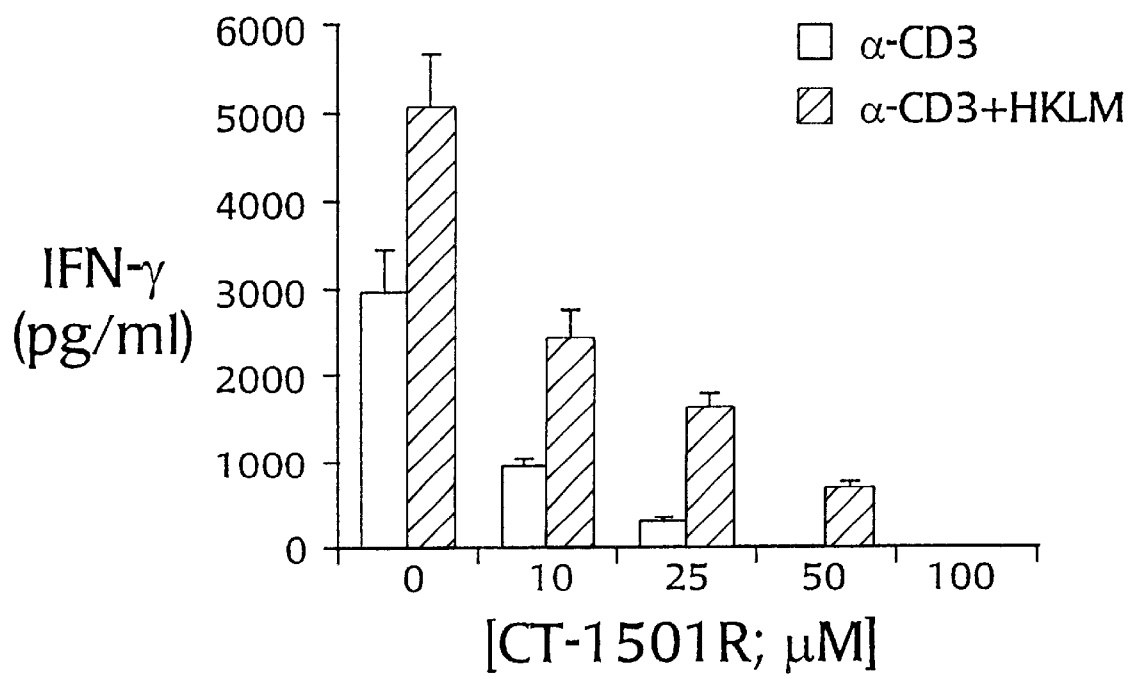
Figure 9:
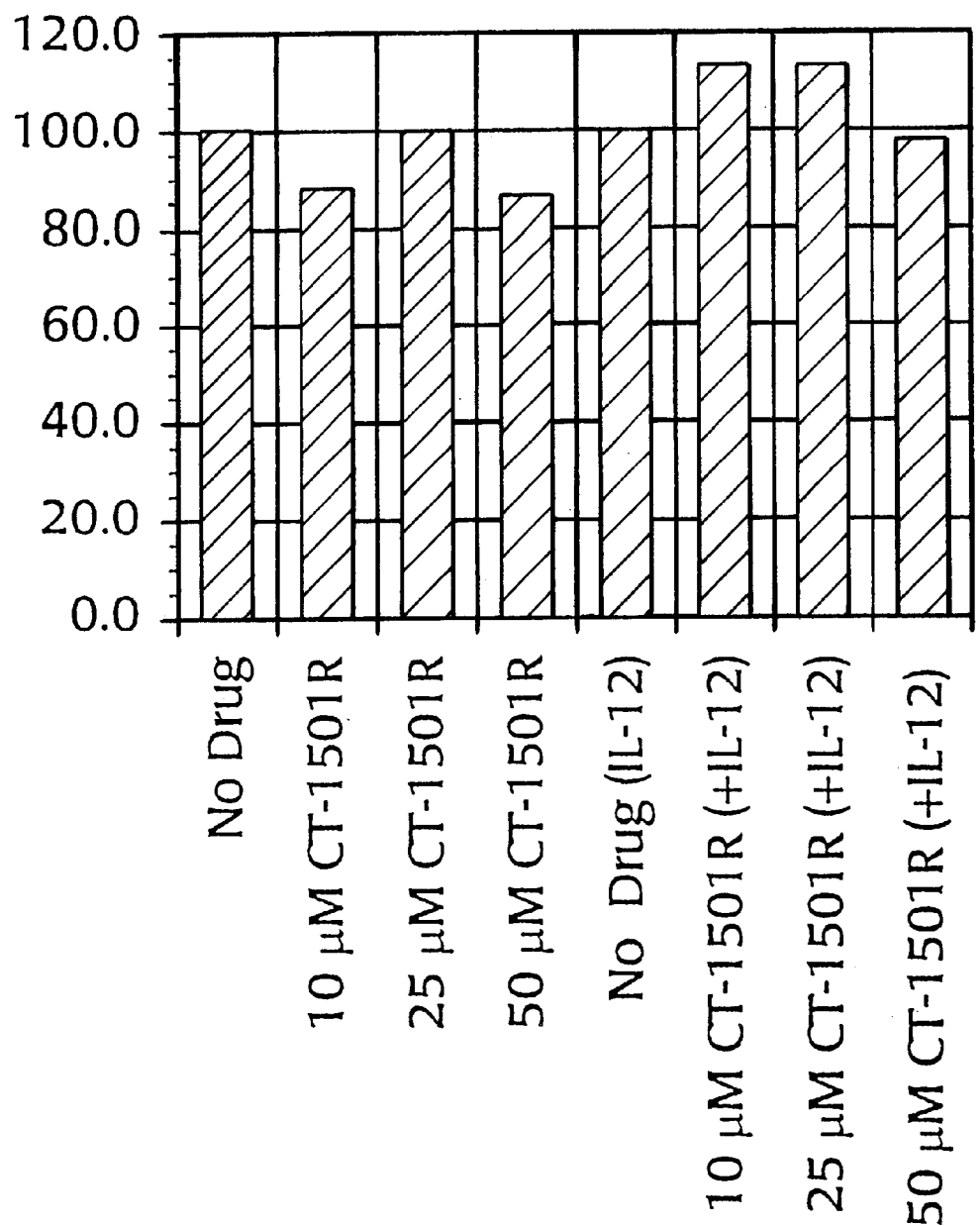
FIG. 9 shows the inability of CT 1501R to effect the viability or recovery of T-cells in culture.
Figure 10:
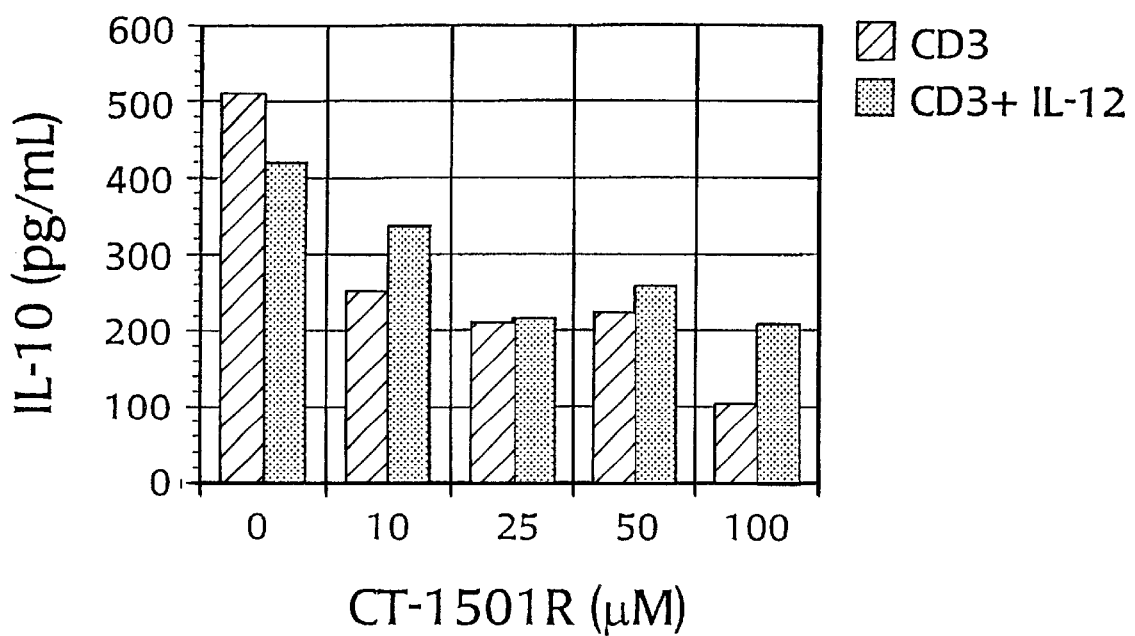
FIG. 10 shows the inability of CT 1501R to enhance IL-10 secretion.

Anti-CD3 stimulated T cells differentiated into Th1 cells, and as expected Th1 cell differentiation was increased in the presence of recombinant IL-12 (FIG. 6a). Strikingly, the presence of CT 1501R during T cell activation inhibited Th1 differentiation, whether or not Th1 maturation had been enhanced by IL-12 (FIG. 6a). CT 1501R also inhibited Th1 differentiation induced by addition of heat killed Listeria monocytogenes (see FIGS. 8a and 8b), which enhances Th1 development by inducing IL-12 secretion from macrophages. CT 1501R did not affect the viability or recovery of T cells after one week of culture (see FIG. 9), consistent with its inability to block lymphocyte activation (FIG. 4c). Furthermore, CT 1501R did not augment Th2 differentiation at the expense of Th1 development, since IL-4 and IL-10 secretion was not enhanced (see FIG. 10, data for IL-10 only).

Comparative Example 1

Inability of Pentoxifylline to Inhibit IL-12 Signaling

This experiment compares the efficacy of Pentoxifylline ("PTX"), [3,7-dimethyl-1-(5-oxohexyl) xanthine], (Sigma, St Louis, Mo.) and CT 1501R to inhibit in vitro Th1 differentiation driven by addition of exogenous IL-12. PTX is a known anti-inflammatory molecule and is known to inhibit induction of EAE in rats. Rott et al., *Eur. J. Immunol.*, 23:1745–1751(1993). It is also known that high doses of PTX inhibit IL-12 secretion in vitro. Moller et al., *Immunology*, 91:197–203 (1997).

The methodology described in Example 7 was also employed in this experiment. Splenic T cells were stimulated with anti-CD3 and IL-12 as above, and incubated with either CT 1501R or PTX as indicated. The levels of IFN-γ produced by T cells stimulated with anti-CD3 and no IL-12 were 5.8 ng/ml (FIG. 6b).

Figure 6B:
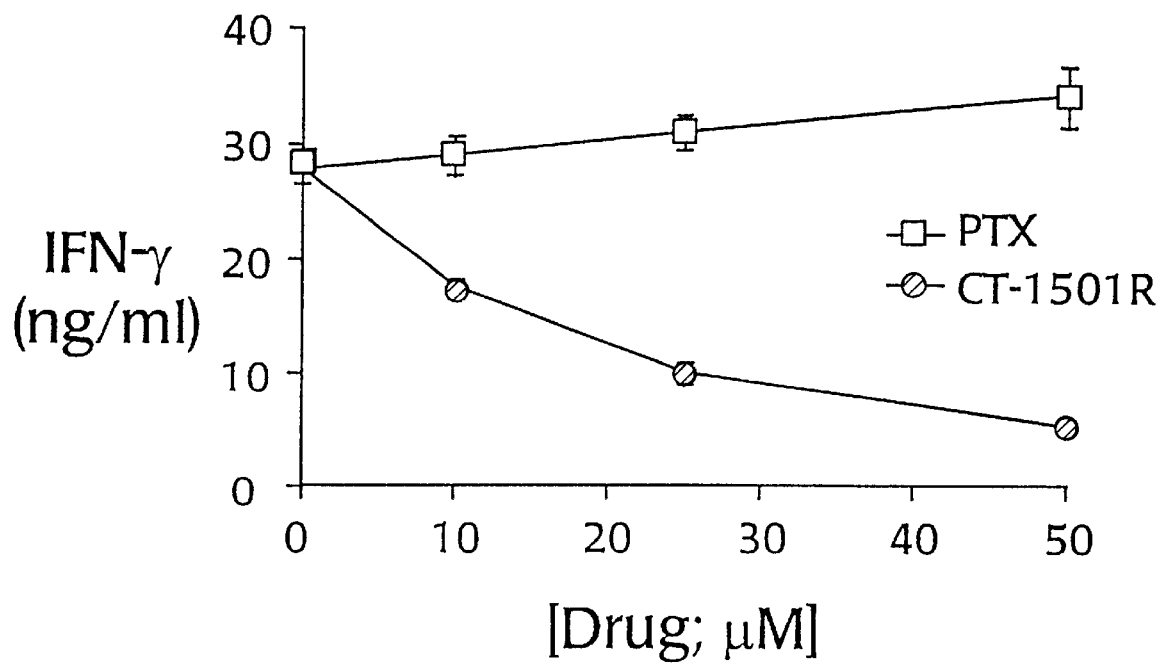
Figure 11A:
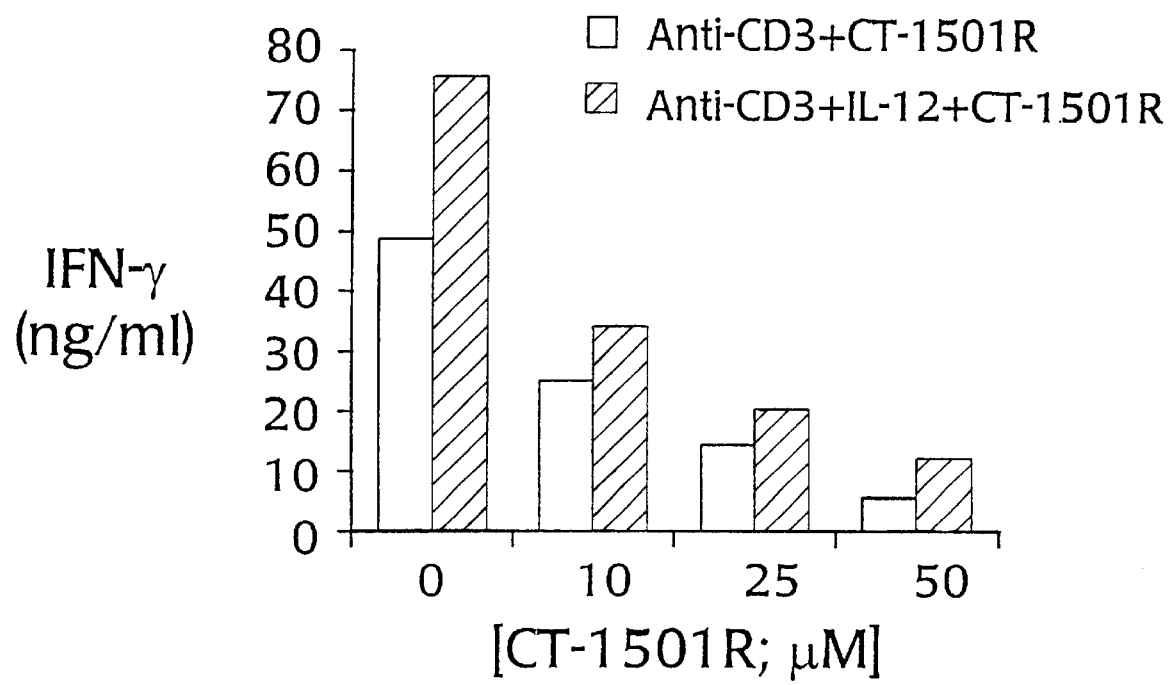
FIGS. 11a and 11b show the inability of (S)-1-(5-hydroxyhexyl)-3,7-dimehylxanthine to effect Th1 cell maturation.
Figure 11B:
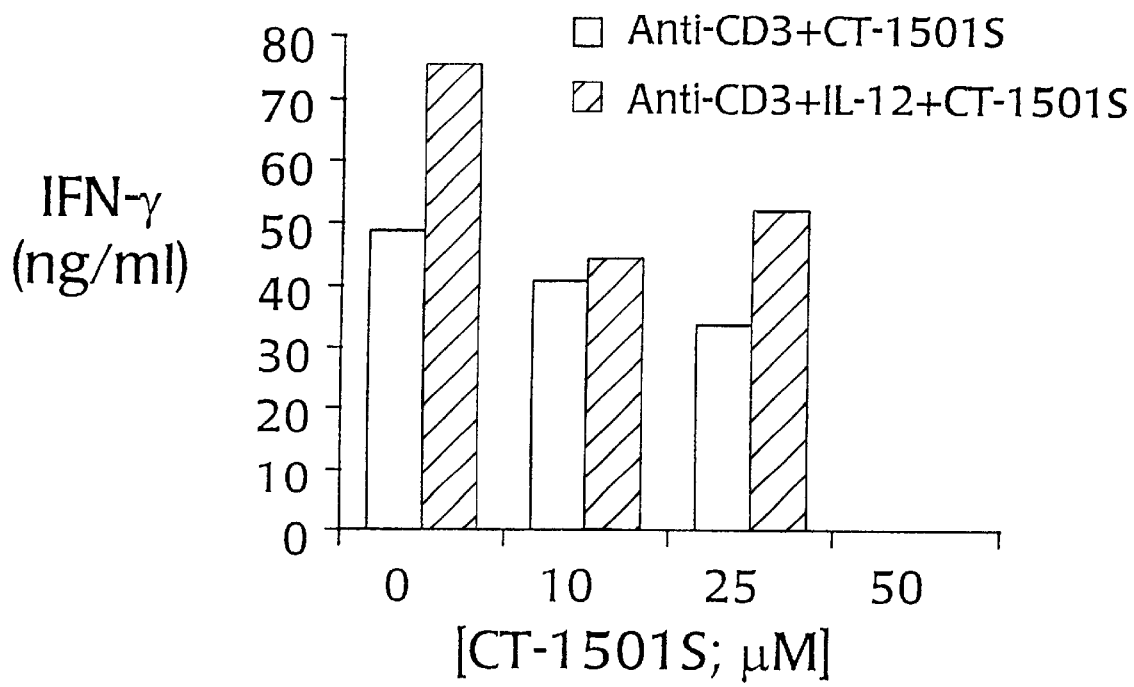

The experiments showed that CT 1501R inhibited Th1 differentiation in a dose-dependent fashion, resulting in a >85% blockade at 50 μM, when cells were stimulated with anti-CD3 and exogenous IL-12 (FIG. 6b). In contrast, equimolar concentrations of PTX had no effect on IL-12 induced Th1 differentiation. Thus, PTX had no effect on IL-12 signaling. Similarly, the stereochemical enantiomer of CT 1501R, CT 1501S, also had no effect on Th1 differentiation, i.e. IL-12 signaling (FIGS. 11a and 11b).

Although PTX is structurally similar to CT 1501R, in this example, CT 1501R, but not PTX, inhibited IL-12-induced Th1 differentiation (FIG. 6B). With regard to inhibition of IL-12 signaling, CT 1501R was also selectively inhibitory when compared to its stereospecific S-enantiomer.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for the purpose of illustration, various modifications may be made without deviating from the spirit and scope of the invention.

What is claimed is:

1. A method of inhibiting Interleukin-12 signaling in a mammal having a CD4+ Th1 cell-mediated inflammatory response, the method comprising administering a signal inhibiting amount of a compound of the following formula:

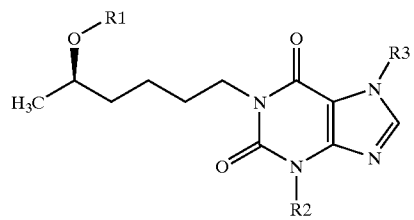

wherein, $R_1$ is $CH_3$, sulfate, phosphate, or salt thereof; $R_2$ is alkyl ($C_{1-12}$), alkoxyalkyl ($C_{1-11}$), dialkoxyalkyl, $CH_2C_6H_5$, —$CH_2$-furan, biotin; and $R_3$ is H, $CH_3$ or $CH_2C_6H_5$.

2. The method of claim 1, wherein $R_2$ is alkyl ($C_{1-12}$), $CH_2C_6H_5$, —$CH_2$-furan, or biotin and $R_3$ is H or methyl.

3. The method of claim 2, wherein $R_2$ is alkyl ($C_{1-12}$), biotin or —$CH_2$-furan.

4. The method of claim 3, wherein $R_1$ is sulfate or phosphate or a salt thereof, and $R_2$ and $R_3$ are $CH_3$.

5. The method of claim 1, wherein the compound is of the following formula:

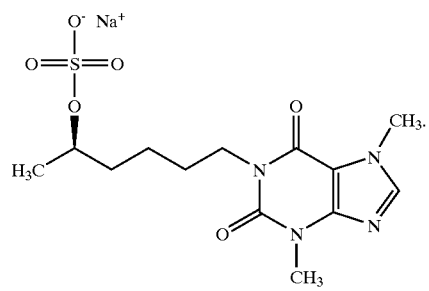

6. The method of claim 1, wherein the compound is of the following formula:

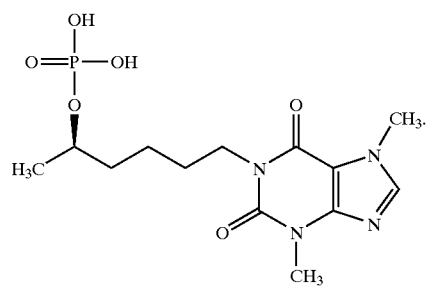

7. A method of inhibiting Interleukin-12 signaling in a mammal having a CD4+ Th1 cell-mediated inflammatory response, the method comprising administering a signal inhibiting amount of a compound of the following formula:

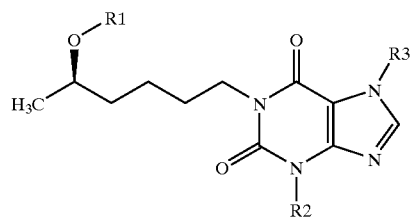

wherein, $R_1$ is H, $CH_3$, sulfate, phosphate, or salt thereof; $R_2$ is alkyl ($C_{1-12}$), alkoxyalkyl ($C_{1-11}$), dialkoxyalkyl, $CH_2C_6H_5$, —$CH_2$-furan, biotin; and $R_3$ is H, $CH_3$ or $CH_2C_6H_5$, provided that when R1 is H, R2 is not alkyl ($C_{1-12}$) and R3 is not CH3.

8. The method of claim 7, wherein a disease condition, which exhibits The CD4+ Th1 cell-mediated inflammatory response, is selected from the group consisting of chronic inflammatory disease, chronic intestinal inflammation, arthritis, psoriasis, asthma, and autoimmune disorders.

9. The method of claim 7, wherein an autoimmune disorder generates the CD4+ Th1 cell-mediated inflammatory response.

10. The method of claim 9, wherein the autoimmune disorder is selected from the group consisting of type-1 insulin dependent diabetes mellitus ("IDDM"), multiple sclerosis, rheumatoid arthritis, inflammatory bowel disease, lupus disorders, and acute graft-versus-host disease.

11. The method of claim 7, wherein the mammal is a human.

* * * * *